United States Patent
Rosenberg et al.

(10) Patent No.: US 11,807,665 B2
(45) Date of Patent: Nov. 7, 2023

(54) DETECTION AND QUANTIFICATION OF GLYCOSYLATED PEPTIDES

(71) Applicant: Regeneron Pharmaceuticals, Inc., Tarrytown, NY (US)

(72) Inventors: Avraham Z. Rosenberg, Passaic, NJ (US); Biao Shen, Dobbs Ferry, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 765 days.

(21) Appl. No.: 16/509,798

(22) Filed: Jul. 12, 2019

(65) Prior Publication Data

US 2020/0017544 A1 Jan. 16, 2020

Related U.S. Application Data

(60) Provisional application No. 62/697,547, filed on Jul. 13, 2018.

(51) Int. Cl.
| | |
|---|---|
| *C07K 1/16* | (2006.01) |
| *B01D 15/30* | (2006.01) |
| *B01D 15/42* | (2006.01) |
| *G01N 33/68* | (2006.01) |

(52) U.S. Cl.
CPC .............. *C07K 1/16* (2013.01); *B01D 15/305* (2013.01); *B01D 15/426* (2013.01); *G01N 33/6848* (2013.01)

(58) Field of Classification Search
None
See application file for complete search history.

(56) References Cited

U.S. PATENT DOCUMENTS

2009/0294362 A1 12/2009 Persson et al.

FOREIGN PATENT DOCUMENTS

| JP | 2015-121539 A2 | 7/2015 |
|---|---|---|
| WO | WO2017037829 A1 | 3/2017 |
| WO | WO2017189357 A3 | 12/2017 |

OTHER PUBLICATIONS

Ley, A, et al. HILIC—an alternative separation technique for glycopeptides, ThermoFisher Scientific, retrieved from internet: file:///C:/Users/xxu/Documents/e-Red%20Folder/16509798/ThermoFisher%202017.pdf (Year: 2017).*
Jandera, P., Stationary and mobile phases in hydrophilic interaction chromatography: a review, Analytics Chimica Acta, 695, 1-25 (Year: 2011).*

(Continued)

*Primary Examiner* — Xiaoyun R Xu
(74) *Attorney, Agent, or Firm* — Kramer Levin Naftalis & Frankel LLP

(57) ABSTRACT

A method of purification and/or separation of glycopeptides and quantitation of same. The method includes contacting a sample comprising glycopeptides to a hydrophilic enrichment substrate under conditions that permit the glycopeptides to bind to the hydrophilic enrichment substrate. The glycopeptides are eluted from the hydrophilic enrichment substrate with an ammonium formate and acetonitrile (ACN) in water solution to create an enriched glycopeptide sample, which may be subjected to analysis to identify specific glycopeptides.

20 Claims, 27 Drawing Sheets

(56) References Cited

OTHER PUBLICATIONS

Zacharias, L.C., HILIC and ERLIC Enrichment of Glycopeptides Derived from Breast and Brain Cancer Cells, Journal of Proteome Research, 15, 3624-3634 (Year: 2016).*
Huang, L. et al. Surface Hydrophilicity and Antifungal Properties of TiO2 Films Coated on a Co—Cr Substrate, BioMed Research International, vol. 2017, Article ID 2054723, 7 pages. https://doi.org/10.1155/2017/2054723 (Year: 2017).*
Akira Kondo et al.; "Characterization of Sialylated and Fucosylated Glycopeptides of [beta]2-glycoprotein I by a Combination of HILIC LC and MALDI MS/MS," vol. 33, No. 6-7, Mar. 1, 2010, pp. 891-902.
Giuseppe Palmisano et al.; "Selective Enrichment of Sialic Acid-containing Glycopeptides Using Titanium Dioxide Chromatography with Analysis by HILIC and Mass Spectrometry," Nature Protocols, vol. 5, No. 12, Nov. 18, 2010, pp. 1974-1982.
Martin R. Larsen et al.; "Characterization of Gel-Separated Glycoproteins Using Two-stop Proteolytic Digestion Combined with Sequential Microcolumns and Mass Spectrometry," Molecular & Cellular Proteomics, vol. 4, No. 2, Feb. 1, 2005, pp. 107-119.
Alagesan Kathirvel et al.; "It is all about the Solvent: on the Importance of the Mobile Phase for ZIC-HILIC Glycopeptide Enrichment," Analytical and Bioanalytical Chemistry, Springer, DE, vol. 409, No. 2, Dec. 1, 2016, pp. 529-538.
International Search Report, PCT Application No. PCT/US2019/041541, Application Filing Date Jul. 12, 2019, dated Sep. 30, 2019.

\* cited by examiner

| Glycan | % Total Glycoforms ||
|---|---|---|
| | Glycopeptide | Released Glycan |
| | 0.51 | 0.10 |
| | 0.44 | ND |
| | 2.50 | 0.26 |
| | 2.46 | 1.60 |
| | 5.43 | 0.30 |
| | 12.25 | 13.09 |
| | 3.75 | ND |
| | 23.57 | 34.12 |
| | 7.66 | 2.41 (1-6) / 3.30 (1-3) } 5.71 |
| | 28.12 | 14.01 (1-6) / 16.16 (1-3) } 30.17 |
| | 2.67 | 1.14 |
| | 10.65 | 11.21 |

FIG. 2

|  | % Peak Areas of Glycan Species | | | |
| --- | --- | --- | --- | --- |
| Glycan | Glycopeptides | | RapiFluor-MS Labeled Glycans | |
|  | Reduced<br>*Dried* | Non-Reduced<br>*Re-digested SPE/Dried* | Original | Out of 100% |
| G0F-GlcNAc | 1.24 | 0.98 | 1.31 | 1.34 |
| G0 | 8.36 | 8.25 | 7.42 | 7.59 |
| G0F | 44.16 | 46.33 | 45.07 | 46.09 |
| Man5 | 1.67 | 1.73 | 1.24 | 1.27 |
| G1F (1-3)-GlcNAc | 0.83 | 0.93 | 0.84 | 0.86 |
| G1 (1-6) | 1.95 | 2.33 | 1.7 | 1.74 |
| G1 (1-3) | 1.27 | 0.96 | 0.83 | 0.85 |
| G1F (1-6) | 24.92 | 24.96 | 24.25 | 24.80 |
| G1F (1-3) | 8.8 | 8.44 | 8.57 | 8.76 |
| G2 | ND | ND | 0.41 | 0.42 |
| G2F | 6.8 | 5.09 | 6.14 | 6.28 |
| %Fucosylation | 86.8 | 86.7 | 86.2 | 88.1 |
| %Galactosylation | 25.7 | 23.9 | 24.6 | 25.2 |

FIG.20B

DETECTION AND QUANTIFICATION OF GLYCOSYLATED PEPTIDES

CROSS-REFERENCE TO RELATED APPLICATION

This application claims the benefit under 35 USC § 119(e) of U.S. Provisional Application No. 62/697,547, filed Jul. 13, 2018, which is incorporated herein by reference in its entirety for all purposes.

FIELD OF THE INVENTION

The present invention pertains to biopharmaceuticals, and relates to the detection and quantification of in vivo post-translational glycosylation of proteins, such as therapeutic antibodies and fragments thereof.

BACKGROUND

Therapeutic monoclonal antibodies (mAbs) are heterogeneous molecules produced in mammalian cells with many product variants, including variants resulting from post-translational modifications (PTMs). N-linked glycosylation is a major PTM in therapeutic antibodies. The characterization of N-linked glycan structures and quantification of individual glycoforms are required by regulatory agencies to define the quality of the drug product, demonstrate lot-to-lot consistency, and ensure control of the manufacturing process. Traditionally, N-linked glycans within antibodies are quantified by enzymatically releasing the glycans from the antibody followed by labeling with fluorescent reagents. Alternatively, the glycosylation can be characterized at the peptide level by analyzing glycopeptides generated from a tryptic digestion of an antibody. However, glycopeptides possessing heterogeneous glycoforms are often not well separated by reverse phase-based liquid chromatography (RPLC), which is traditionally used for peptide mapping. In addition, online mass spectrometry (MS) induced in-source fragmentation of the sugar chain in glycopeptides can produce truncated glycoform artifacts, which compromise the accurate quantification of the relative abundance of the different glycoforms using MS.

BRIEF SUMMARY OF THE INVENTION

In one aspect, the present invention provides a method of purification and/or separation of glycopeptides, in which the method comprises: (a) contacting a sample comprising glycopeptides to a hydrophilic enrichment substrate under conditions that permit the glycopeptides to bind to the hydrophilic enrichment substrate; (b) washing the hydrophilic enrichment substrate to remove non-glycopeptide contaminants from the hydrophilic enrichment substrate; and (c) eluting the glycopeptides from the hydrophilic enrichment substrate with an ammonium formate and acetonitrile (ACN) in water solution, thereby creating an enriched glycopeptide sample. Optionally, the method includes applying the enriched glycopeptide sample to a separation column and eluting the glycopeptides from the separation column.

In some embodiments, the hydrophilic enrichment substrate comprises a solid phase extraction (SPE) chromatography substrate.

In some embodiments, the hydrophilic enrichment substrate comprises a silica-based aminopropyl sorbent material.

In some embodiments, the ammonium formate and ACN in water solution comprises about 100-400 mM ammonium formate and about 2.5% to about 10% ACN in water.

In some embodiments, the ammonium formate ACN solution comprises 200 mM ammonium formate and 5% ACN in water.

In some embodiments, the hydrophilic enrichment substrate is washed with a formic acid and ACN wash solution comprising 0.5% to about 5% formic acid by volume and about 85% to about 95% ACN by volume with the remainder water to remove non-glycopeptide contaminants.

In some embodiments, the formic acid and ACN wash solution comprises 1% formic acid, 9% $H_2O$, 90% ACN by volume.

In some embodiments, the separation column comprises a hydrophilic interaction (HILIC) column.

In some embodiments, eluting the glycopeptide from the separation column further comprises separating the glycopeptides into one or more fractions.

In some embodiments, separating the glycopeptides into one or more fractions comprises applying a mobile phase gradient to the separation column.

In some embodiments, the mobile phase gradient is 10 mM ammonium formate, pH 4.5 to 90% ACN with 10 mM ammonium formate, pH 4.5.

In some embodiments, the mobile phase gradient is 0.05% TFA in $H_2O$ or 0.045% TFA in ACN.

In some embodiments, the method further includes identifying the glycopeptides present in one or more of the fractions.

In some embodiments, the method further includes identifying a glycan associated with the glycopeptides present in one or more of the fractions.

In some embodiments, the glycan comprises an N-glycan.

In some embodiments, the glycopeptides are obtained from a monoclonal antibody.

In some embodiments, the monoclonal antibody is of isotype IgG1, IgG2, IgG3, IgG4, or mixed isotype.

In some embodiments, the method further includes digesting the monoclonal antibody with a protease.

In some embodiments, the protease comprises trypsin.

In some embodiments, the method further includes performing mass spectrometric analysis on the eluted glycopeptides.

In some embodiments, the method further includes glycosylation profiling at a glycopeptide level of the eluted glycopeptides.

In some embodiments, the method further includes pre-washing the hydrophilic enrichment substrate with an acetonitrile (ACN) in water solution.

In some embodiments, the method further includes diluting a sample comprising glycopeptides in an ACN in water solution prior to contact with the hydrophilic enrichment substrate.

DESCRIPTION OF THE FIGURES

FIG. 2 shows a table showing the results of the method of glycopeptide quantitation shown in the work-flow of FIG. 1, compared with the quantitation of released glycans; i.e., one based on detection of glycopeptides and the other based on the detection of released glycan.

FIGS. 20A and 20B show a set of traces and a table demonstrating similar glycoform quantitations using reduced and non-reduced mAb3 tryptic digests by glycopeptide and released glycan analyses.

DETAILED DESCRIPTION OF THE INVENTION

Figure 1:
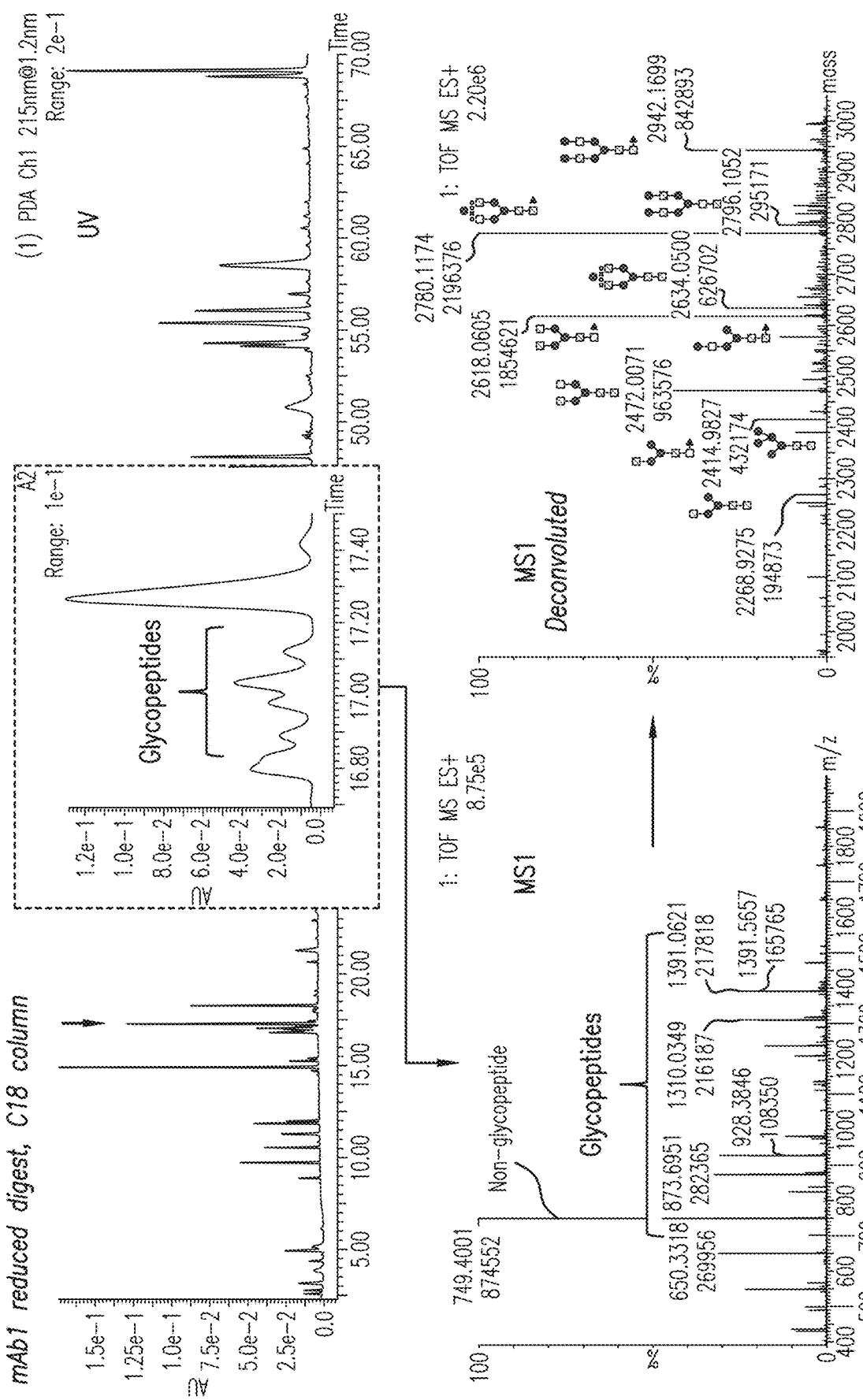
FIG. 1 shows a schematic work-flow diagram illustrating current standard methods of glycopeptide quantitation by liquid chromatography coupled with mass spectrometry (LC/MS).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.)

Although any methods and materials similar or equivalent to those described herein can be used in the practice or testing of the present invention, the preferred methods and materials are now described. All patents, applications and non-patent publications mentioned in this specification are incorporated herein by reference in their entireties.

Abbreviations Used Herein
 PTMs: Post-translational Modifications
 RP-LC-MS/MS: Reversed Phase Liquid Chromatography Tandem Mass Spectrometry
  mAb: Monoclonal Antibody
  IgG: Immunoglobulin G
  LC: Light Chain
  HC: Heavy Chain
  MS: Mass Spectrometry
  SPE: Solid Phase Extraction
  HILIC: Hydrophilic Interaction Liquid Chromatography
  UV: Ultraviolet
  TFA: Trifluoroacetic Acid
  ACN: Acetonitrile
 Definitions The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR).

Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains*, 27(1) Dev. Comp. Immunol. 55-77 (2003); and M. Potter, *Structural correlates of immunoglobulin diversity*, 2(1) Surv. Immunol. Res. 27-42 (1983).

The term antibody also encompasses "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527 (Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et at. (1993) 90 PNAS U.S.A. 6444-6448; and Poljak et at. (1994) 2 Structure 1121-1123).

Moreover, antibodies and antigen-binding fragments thereof can be obtained using standard recombinant DNA techniques commonly known in the art (see Sambrook et al., 1989).

The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

The term as used herein, "glycopeptide/glycoprotein" is a modified peptide/protein, during or after their synthesis, with covalently bonded carbohydrates or glycan. In certain embodiments, a glycopeptide is obtained from a monoclonal antibody, for example, from a protease digest of a monoclonal antibody.

The term as used herein, "glycan" is a compound comprising one or more sugar units which commonly include glucose (Glc), galactose (Gal), mannose (Man), fucose (Fuc), N-acetylgalactosamine (GalNAc), N-acetylglucosamine (GlcNAc) and N-acetylneuraminic acid (NeuNAc) (Frank Kjeldsen, et al. Anal. Chem. 2003, 75, 2355-2361). The glycan moiety in glycoprotein, such as a monoclonal antibody, is an important character to identify its function or cellular location. For example, a specific monoclonal antibody is modified with specific glycan moiety.

The term "hydrophilic interaction chromatography" or HILIC is intended to include a process employing a hydrophilic stationary phase and a hydrophobic organic mobile phase in which hydrophilic compounds are retained longer than hydrophobic compounds. In certain embodiments, the process utilizes a water-miscible solvent mobile phase.

The term "sample," as used herein, refers to a mixture of molecules that comprises at least an analyte molecule, e.g., glycopeptide, such as obtained from a monoclonal antibody, that is subjected to manipulation in accordance with the methods of the invention, including, for example, separating, analyzing, extracting, concentrating or profiling.

The terms "analysis" or "analyzing," as used herein, are used interchangeably and refer to any of the various methods of separating, detecting, isolating, purifying, solubilizing, detecting and/or characterizing molecules of interest (e.g., glycoprotein). Examples include, but are not limited to, solid phase extraction, solid phase micro extraction, electrophoresis, mass spectrometry, e.g., SPE HILIC, MALDI-MS or ESI, liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

The term "profiling," as used herein, refers to any of various methods of analysis which are used in combination to provide the content, composition, or characteristic ratio of glycopeptides in a sample.

A "hydrophilic enrichment substrate," as used herein, is a chromatographic material that preferentially binds hydrophilic materials under conditions that permit the binding, for example pH, ionic strength, etc. In some embodiments, a hydrophilic enrichment substrate is used for SPE.

The term "chromatographic surface," as used herein, includes a surface which is exposed to a sample or analytes. A chromatographic surface can be chemically modified, functionalized or activated or have a microstructure, e.g. a pore. In certain embodiments, the chromatographic surface can be hydrophobic, hydrophilic (polar) or ionic. In other embodiments, the chromatographic surface is fully porous, superficially porous or non-porous.

The term "chromatographic core," as used herein, includes a chromatographic material, including but not limited to an organic material such as silica, in the form of a particle, a monolith or another suitable structure which forms an internal portion of the materials of the invention. In certain aspects, the surface of the chromatographic core represents the chromatographic surface, or represents a material encased by a chromatographic surface, as defined herein. The chromatographic surface material may be disposed on or bonded to or annealed to the chromatographic core in such a way that a discrete or distinct transition is discernible or may be bound to the chromatographic core in such a way as to blend with the surface of the chromatographic core resulting in a gradation of materials and no discrete internal core surface. In certain aspects, the chromatographic surface material may be the same or different from the material of the chromatographic core and may exhibit different physical or physiochemical properties from the chromatographic core, including, but not limited to, pore volume, surface area, average pore diameter, carbon content or hydrolytic pH stability.

The term "hydrophilic," as used herein, describes having an affinity for, attracting, adsorbing or absorbing water.

The term "hydrophobic," as used herein, describes lacking an affinity for, repelling, or failing to adsorb or absorb water.

"Solid phase extraction" or "SPE" is a chromatographic technique often used in conjunction with quantitative chemical analysis, for example, high performance liquid chromatography (HPLC), or gas chromatography (GC). The goal of SPE is to isolate target analytes from a complex sample matrix containing unwanted contaminants. The isolated target analytes are recovered in a solution that is compatible with quantitative analysis. This final solution containing the target compound can be directly used for analysis or evaporated and reconstituted in another solution of a lesser volume for the purpose of further concentrating the target compound, making it more amenable to detection and measurement.

"Chromatography," as used herein, refers to the process of separating a mixture, for example a mixture containing glycopeptides. It involves passing a mixture through a stationary phase, which separates molecules of interest from other molecules in the mixture and allows one or more molecules of interest to be isolated. Examples of methods of chromatographic separation include capillary-action chromatography, such as paper chromatography, thin layer chromatography (TLC), column chromatography, fast protein liquid chromatography (FPLC), nano-reversed phase liquid chromatography, ion exchange chromatography, gel chromatography, such as gel filtration chromatography, size exclusion chromatography, affinity chromatography, high performance liquid chromatography (HPLC), hydrophilic interaction liquid chromatography (HILIC), and reverse phase high performance liquid chromatography (RP-HPLC) amongst others.

"Contacting," as used herein, includes bringing together at least two substances in solution or solid phase, for example contacting a stationary phase of a chromatography material with a sample.

General Description

Monoclonal antibodies (MAbs) have emerged as effective biopharmaceuticals for cancer and other chronic diseases due to the specificity of these drugs toward target antigens, for example, by activating the immune system to kill tumor cells, blocking the signal transduction of tumor cells to proliferate, carrying drugs to tumor cells or as radiation targets. The glycosylation of immunoglobulins influences both their physiochemical properties, and their cell-mediated effector functions such as complement binding and activation. These biological functions may be dependent not only on the presence or absence of N-linked oligosaccharides but also on the specific structure of the oligosaccharides. Furthermore, N-glycosylation of antibodies is routinely characterized in the manufacturing of biopharmaceuticals. In particular, the glycan profile of a monoclonal antibody is sometimes defined as a critical quality attribute, since it can be a measure of efficacy, immunogenicity, and manufacturing conditions. It is therefore important that approaches for glycan analysis exhibit high sensitivity to facilitate detailed characterization. In the manufacture of therapeutic monoclonal antibodies, the site-specific N-glycosylation and assessment of N-glycan site occupancy are important. Thus, there is a need for high efficiency/high resolution methods to separate glycopeptides obtained from monoclonal antibodies. The disclosed invention meets that need.

Figure 22:
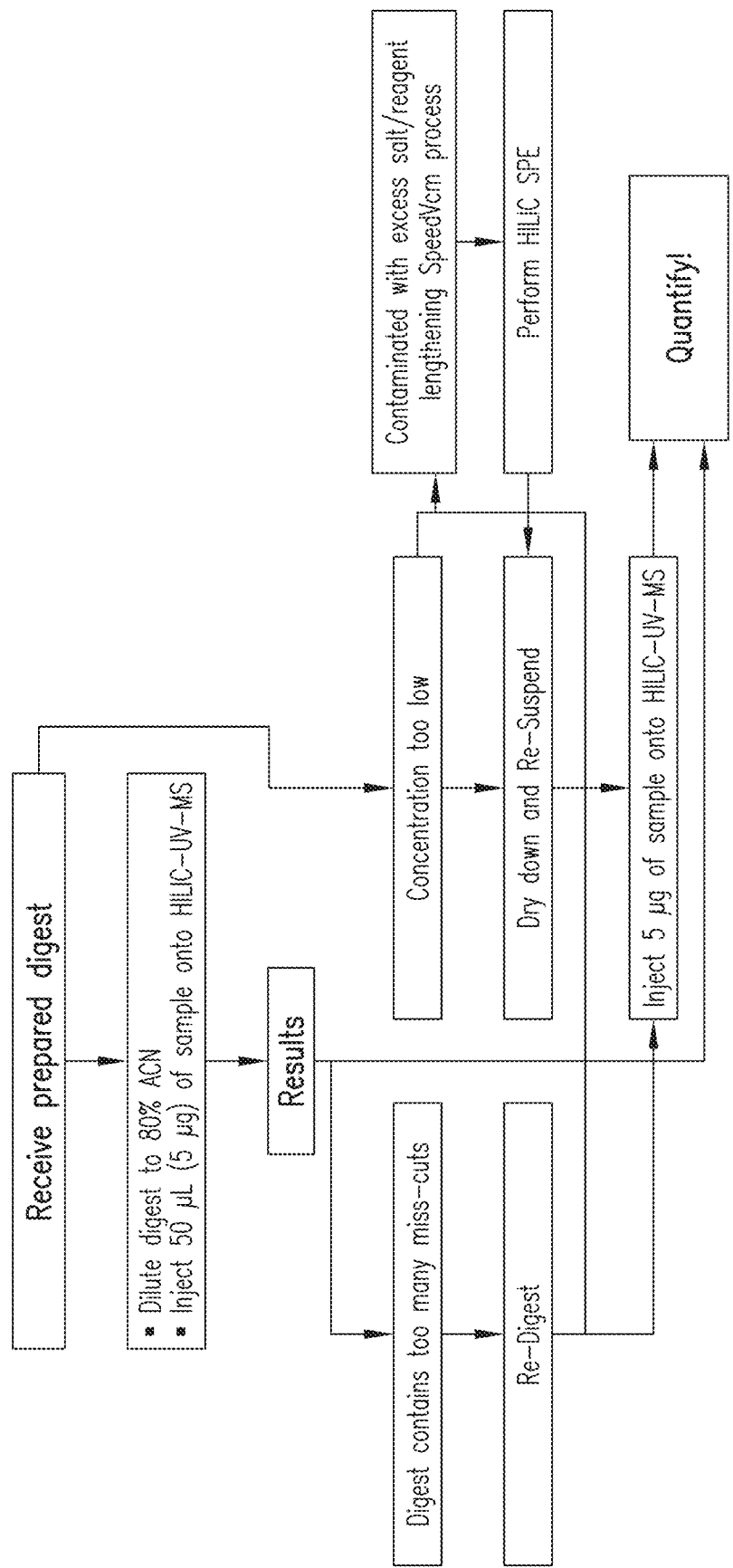
FIG. 22 shows a schematic work-flow diagram illustrating methods of glycopeptide quantitation that include the methods disclosed herein.

Disclosed herein is a new method for glycopeptide analysis and quantification in which a solid phase extraction (SPE) is coupled with a hydrophilic interaction liquid chromatography (HILIC) column to separate glycosylated and non-glycosylated tryptic peptides. In various embodiments, these separation techniques are coupled with ultraviolet (UV) detection and online Mass Spectrometry (MS) detection to elucidate the glycan structures. In some methods, glycan characterization relies on releasing glycans from peptide chains and then analyzing them separately from the peptides (see, e.g., FIGS. 1-3). Because glycans are not suitable for UV detection, the released glycans are often labeled with a fluorophore tag, e.g. anthranilamide, anthranilic acid or 2-aminopyridine, for fluorescence detection or a molecule, e.g. procainamide, with significant basicity so as to enable MS detection. However, this approach to glycan analysis only gives a global assessment of glycosylation. In particular, site-specific information about glycans is lost due to this workflow relying on a release procedure. In contrast, in the disclosed method, the isolated glycopeptides are separated based on differences in glycoform structure within the same chromatographic separation. Furthermore, the separation of glycopeptides with different glycan isomers, which was achieved using the HILIC column, was not observed using standard RP-LC methods (see, e.g., FIGS. 1-3). By optimizing the sample preparation conditions for HILIC, including dilution, vacuum drying, and/or solid phase extraction (SPE), a workflow was developed that enables the analysis of glycopeptides from different types of peptide mapping sample preparations (see, e.g., FIG. 22). As disclosed herein, the inventors have demonstrated that the method and workflow is suitable for identification and quantification of the relative levels of individual glycoforms in an antibody at the peptide level using UV detection coupled with online MS detection (see, e.g., FIGS. 4 and 22).

The methods disclosed herein include purification and/or separation and/or analysis of glycopeptides, for example, glycopeptides obtained from a monoclonal antibody, such as an antibody that has been digested with one or more proteases. The disclosed methods provide improved results of separation and analysis and the ability to study glycans while they are still covalently linked to their antibody fragments. This peptide-level analysis of glycoforms also provides the benefit in biopharmaceutical characterization in that a single sample can be utilized for reversed phase peptide mapping, e.g. a trypsin digest, and HILIC-based glycopeptide mapping. Moreover, preserving the linkage between the glycan and peptide/protein facilitates the UV and MS detection based on the proteinaceous component of the glycopeptide, for example, removing the necessity of labeling freed glycans.

In certain embodiments, the methods include contacting a sample that includes glycopeptides with a hydrophilic enrichment substrate under conditions that permit and/or cause the glycopeptides to bind to the hydrophilic enrichment substrate. Once the sample is loaded onto the hydrophilic enrichment substrate, a series of tailored washing and elution solutions may be passed over the hydrophilic enrichment substrate to separate contaminants from glycopeptides, and then to collect the glycopeptides for further analysis. In some embodiments, the hydrophilic enrichment substrate is washed to remove non-glycopeptide contaminants from the sample. Thus, to a significant degree glycopeptides are enriched on the hydrophilic enrichment substrate, such as on the chromatographic surface of the hydrophilic enrichment substrate. In certain embodiments, a hydrophilic enrichment substrate comprises a silica-based aminopropyl sorbent material. In certain embodiments, the hydrophilic enrichment substrate is configured for solid phase extraction (SPE).

Devices designed for SPE typically include a chromatographic sorbent (for example, a hydrophilic enrichment substrate, such as a silica-based aminopropyl sorbent) which allows the user to preferentially retain target components, in this case glycopeptides. SPE devices typically include a sample holding reservoir, a means for containing the sorbent, and a fluid conduit, or spout for directing the fluids exiting the device into suitable collection containers. The SPE device may be in a single well format, which is convenient and cost effective for preparing a small number of samples, or a multi-well format, which is well suited for preparing large numbers of samples in parallel. Multi-well formats are commonly used with robotic fluid dispensing systems. Typical multi-well formats include 48-, 96-, and 384-well standard plate formats. Fluids are usually forced through the SPE device and into the collection containers, either by drawing a vacuum across the device with a specially designed vacuum manifold, or by using centrifugal or gravitational force. Centrifugal force is generated by placing the SPE device, together with a suitable collection tray, into a centrifuge specifically designed for the intended purpose. It is advantageous for an SPE device to have a high capacity for retaining target compounds of a wide range of chromatographic polarities, to be capable of maintaining target compound retention as sample contaminants are washed to waste, and then to provide the capability to elute target compounds in as small an elution volume as possible, thereby maximizing the degree of target compound concentration obtained during SPE.

A variety of solid phase extraction devices can be used in accordance with the disclosed methods. In one embodiment, the SPE device is selected from the group consisting of micro elution plates, chromatographic columns, thin layer plates, sample cleanup devices, injection cartridges, microtiter plates and chromatographic preparatory devices.

Silica-based aminopropyl sorbent materials, including SPE materials, are known in the art and can be obtained commercially, for example from Waters Corporation, such as in the form of a GlycoWorks HILIC SPE plate (see, for example U.S. Pat. Nos. 6,723,236, 7,052,611, and 7,192,525). In some embodiments, the hydrophilic enrichment substrate is prepared for the addition of the sample by washing, e.g. a prewashing step. In some embodiments, the hydrophilic enrichment substrate is washed prior to contact with the glycopeptide sample. In some embodiments, the hydrophilic enrichment substrate is washed with water ($H_2O$) and/or an ACN solution (e.g. ACN in water), such as an about 60% to about 95% ACN solution by volume, for example an about 60%, 65%, 70%, 75%, 80%, 85%, 90%, or 95% ACN solution by volume, with the remainder water.

In various embodiments, the hydrophilic enrichment substrate is contacted with a sample containing glycopeptide for enrichment. With regard to the sample solution, it will include the glycopeptides dissolved in a solvent in which the glycopeptides are soluble, and in which the glycopeptides will bind to the hydrophilic enrichment substrate. Preferably, the binding is strong, resulting in the binding of a substantial portion of the glycopeptides. In some cases, substantially all of the glycopeptides will be bound. In various embodiments, the solvent is an aqueous solution, typically containing a buffer, salt, and/or surfactants to solubilize and stabilize the glycopeptides. In some embodiments, the glycopeptide sample is a solution of about 60% ACN to 90% ACN and 10% to about 40% water with about 0.1% to about 0.5% TFA by volume, such as about 80:20 ACN:Water (v/v) with 0.2% TFA. A low pH may be used to maintain peptide solubility in highly organic solvent, for example a solution with a pH below about 6.5, such as below about 6.5, 6.0, 5.5, 5.0, 4.5, 4.0, 3.5 or 3.0.

The hydrophilic enrichment substrate is then washed to remove contaminants, such as non-glycosylated peptides that do not significantly bind to the hydrophilic enrichment substrate. Such contaminants may be discarded. In some embodiments, the hydrophilic enrichment substrate is washed with an acid and acetonitrile (ACN) in water ($H_2O$) solution, such as a formic acid and/or trifluoroacetic acid (TFA) and acetonitrile (ACN) in water ($H_2O$) solution. In certain embodiments, the formic acid and ACN in water solution includes about 0.5% to about 5% formic acid by volume and about 85% to about 95% ACN by volume with the remainder water, for example about 0.5%, 1.0%, 1.5%, 2.0%, 2.5%, 3.0%, 3.5%, 4.0%, 4.5%, or 5.0% formic acid by volume and about 80%, 85%, 90%, or 95% ACN by volume. In certain embodiments, the TFA and ACN in water solution includes about 0.5% to about 5% TFA by volume and about 85% to about 95% ACN by volume with the remainder water, for example about 0.5%, 1.0%, 1.5%, 2.0%, 2.5%, 3.0%, 3.5%, 4.0%, 4.5%, or 5.0% TFA by volume and about 80%, 85%, 90%, or 95% ACN by volume. In a certain example, the wash solution is a 1% Formic Acid, 9% $H_2O$, 90% ACN solution by volume. In a certain example, the wash solution is a 1% TFA, 9% $H_2O$, 90% ACN solution by volume.

Once the contaminants have been removed, the hydrophilic enrichment substrate is contacted with an elution solution to elute the glycopeptides from the hydrophilic enrichment substrate. Silica-based aminopropyl sorbent possesses a weakly basic surface and potential for anion exchange. However, the relative and total recovery of glycopeptides from a silica-based aminopropyl sorbent could be particularly sensitive to elution conditions. Biased recovery, or speciation, can be problematic for a sample preparation procedure. In addition to not providing an accurate representation of the species present in the sample, it can be indicative of a method that is not robust and that the relative abundance profiles obtained may not be reproducibly determined, particularly with respect to the most poorly recovered species. For example, for the recovery of derivatized glycans, as opposed to the glycopeptides that are the subject of this disclosure, it is recommended that ammonium acetate in ACN be used as the elution solution. However, in the case of glycopeptides, ammonium acetate in ACN does not yield a good result. Thus, in certain embodiments, the glycopeptides are eluted from the silica-based aminopropyl sorbent with an ammonium formate and ACN in water solution. In some embodiments, the ammonium formate and ACN in water solution includes about 100-400 mM ammonium formate and about 2.5 to about 10% ACN, such as about 100 mM ammonium formate, about 150 mM ammonium formate, about 200 mM ammonium formate, about 250 mM ammonium formate, about 300 mM ammonium formate, about 350 mM ammonium formate, or about 400 mM ammonium formate and about 2.5%, 3.0%, 3.5%, 4.0%, 4.5%, 5.0%, 5.5%, 6.0% 6.5%, 7.0%, 7.5%, 8.0%, 8.5%, 9.0%, 9.5%, or 10.0%, ACN. In a specific example the ammonium formate and ACN in water solution includes about 200 mM ammonium formate and about 5% ACN.

Once the glycopeptides are eluted from the hydrophilic enrichment substrate, the resulting enriched glycopeptide sample may be subjected to further separation and analysis, for example chromatography and/or mass spec analysis. In embodiments, the enriched glycopeptide sample is applied to a separation column and subsequently eluted from the separation column, for example using a mobile phase gradient to resolve the individual species of glycopeptides.

In some embodiments, solvent gradients, step elutions and/or multidimensional elution are performed to elute and/or separate the glycopeptides from the separation column. The use of gradients is well known in the art of chromatography. The basic principle involves adsorbing an analyte to the separation column and then eluting with a desorption solvent gradient. The gradient refers to the changing of at least one characteristic of the solvent, e.g., change in pH, ionic strength, polarity, or the concentration of some agent that influences the strength of the binding interaction.

Gradients used can be gradual or can be added in step. In one embodiment, two or more boluses of desorption solvent varying in one or more dimension are employed. For example, the two or more boluses can vary in pH, ionic strength, hydrophobicity, or the like. A wash solution, if used, may be selected such that it will remove non-desired contaminants with minimal loss or damage to the bound glycopeptides. The properties of the wash solution may be intermediate between that of the sample and desorption solutions. The solvents, for example in an elution gradient, are chosen to be compatible with the glycopeptides and the ultimate detection method. Generally, the solvents used are known conventional solvents. In various embodiments, solvents from which a suitable solvent can be selected include ammonium hydroxide, triethylamine, diammonium phosphate, methylene chloride, acetonitrile (with or without small amounts of basic or acidic modifiers), methanol (containing larger amount of modifier, e.g. acetic acid or triethylamine, or mixtures of water with either methanol or acetonitrile), ethyl acetate, chloroform, hexane, isopropanol, acetone, alkaline buffer, high ionic strength buffer, acidic buffer, strong acids, strong bases, organic mixtures with acids/bases, acidic or basic methanol, tetrahydrofuran and water.

Liquid chromatography, including HPLC, can be used to analyze structures, such as glycopeptides. Various forms of liquid chromatography can be used to study these structures, including anion-exchange chromatography, reversed-phase HPLC, size-exclusion chromatography, high-performance anion-exchange chromatography, and normal phase (NP) chromatography, including NP-HPLC (see, e.g., Alpert et al., J. Chromatogr. A 676:191-202 (1994)). Hydrophilic interaction chromatography (HILIC) is a variant of NP-HPLC that can be performed with partially aqueous mobile phases, permitting normal-phase separation of peptides, carbohydrates, nucleic acids, and many proteins. The elution order for HILIC is least polar to most polar, the opposite of that in reversed-phase HPLC. HPLC can be performed, e.g., on an HPLC system from Waters (e.g., Waters 2695 Alliance HPLC system), Agilent, Perkin Elmer, Gilson, etc.

NP-HPLC, preferably HILIC, is a particularly useful form of HPLC that can be used in the methods described herein. NP-HPLC separates analytes based on polar interactions between the analytes and the stationary phase (e.g., substrate). The polar analyte associates with and is retained by the polar stationary phase. Adsorption strengths increase with increase in analyte polarity, and the interaction between the polar analyte and the polar stationary phase (relative to the mobile phase) increases the elution time. Use of more polar solvents in the mobile phase will decrease the retention time of the analytes while more hydrophobic solvents tend to increase retention times.

Various types of substrates can be used with NP-HPLC, e.g., for column chromatography, including silica, amino, amide, cellulose, cyclodextrin and polystyrene substrates. Examples of useful substrates, e.g., that can be used in column chromatography, include: polySulfoethyl Aspartamide (e.g., from PolyLC), a sulfobetaine substrate, e.g., ZIC®-HILIC (e.g., from SeQuant), POROS® HS (e.g., from Applied Biosystems), POROS® S (e.g., from Applied Biosystems), PolyHydroethyl Aspartamide (e.g., from PolyLC), Zorbax 300 SCX (e.g., from Agilent), PolyGLYCOPLEX® (e.g., from PolyLC), Amide-80 (e.g., from Tosohaas), TSK GEL® Amide-80 (e.g., from Tosohaas), Polyhydroxyethyl A (e.g., from PolyLC), Glyco-Sep-N (e.g., from Oxford GlycoSciences), and Atlantis HILIC (e.g., from Waters). Columns that can be used in the disclosed methods include columns that utilize one or more of the following functional groups: carbamoyl groups, sulfopropyl groups, sulfoethyl groups (e.g., poly (2-sulfoethyl aspartamide)), hydroxyethyl groups (e.g., poly (2-hydroxyethyl aspartamide)) and aromatic sulfonic acid groups.

The mobile phase used may include buffers with and without ion pairing agents, e.g., acetonitrile and water. Ion pairing agents include formate, acetate, TFA and salts. Gradients of the buffers can be used, e.g., if two buffers are used, the concentration or percentage of the first buffer can decrease while the concentration or percentage of the second buffer increases over the course of the chromatography run. For example, the percentage of the first buffer can decrease from about 100%, about 99%, about 95%, about 90%, about 85%, about 80%, about 75%, about 70%, about 65%, about 60%, about 50%, about 45%, or about 40% to about 0%, about 1%, about 5%, about 10%, about 15%, about 20%, about 25%, about 30%, about 35%, or about 40% over the course of the chromatography run. As another example, the percentage of the second buffer can increase from about 0%, about 1%, about 5%, about 10%, about 15%, about 20%, about 25%, about 30%, about 35%, or about 40% to about 100%, about 99%, about 95%, about 90%, about 85%, about 80%, about 75%, about 70%, about 65%, about 60%, about 50%, about 45%, or about 40% over the course of the same run. Optionally, the concentration or percentage of the first and second buffer can return to their starting values at the end of the chromatography run. As an example, the percentage of the first buffer can change in five steps from 85% to 63% to 59% to 10% to 85%; while the percentage of the second buffer in the same steps changes from 15% to 37% to 41% to 90% to 15%. The percentages can change gradually as a linear gradient or in a non-linear (e.g., stepwise)

fashion. For example, the gradient can be multiphasic, e.g., biphasic, triphasic, etc. In preferred embodiments, the methods described herein use a decreasing acetonitrile buffer gradient which corresponds to increasing polarity of the mobile phase without the use of ion pairing agents.

The column temperature can be maintained at a constant temperature throughout the chromatography run, e.g., using a commercial column heater. In some embodiments, the column is maintained at a temperature between about 18° C. to about 70° C., e.g., about 30° C. to about 60° C., about 40° C. to about 50° C., e.g., at about 20° C., about 25° C., about 30° C., about 35° C., about 40° C., about 45° C., about 50° C., about 55° C., about 60° C., about 65° C., or about 70° C. A preferred temperature is about 45° C.

The flow rate of the mobile phase can be between about 0 to about 100 ml/min. For analytical proposes, flow rates typically range from 0 to 10 ml/min, for preparative HPLC, flow rates in excess of 100 ml/min can be used. For example, the flow rate can be about 0.5, about 1, about 1.5, about 2, about 2.5, about 3, about 3.5, about 4, about 4.5, or about 5 ml/min. Substituting a column having the same packing, the same length, but a smaller diameter requires a reduction in the flow rate in order to retain the same retention time and resolution for peaks as seen with a column of wider diameter. Preferably, a flow rate equivalent to about 1 ml/min in a 4.6×100 mm, 5 µm column is used.

The run time can be between about 15 to about 240 minutes, e.g., about 20 to about 70 min, about 30 to about 60 min, about 40 to about 90 min, about 50 min to about 100 min, about 60 to about 120 min, about 50 to about 80 min.

The NP-HPLC can be adjusted to be performed on a nanoscale, e.g., using columns with an inner diameter of about 75 µm (see, e.g., Wuhrer et al., Anal. Chem. 76:833-838 (2004); Wuhrer et al., Internat. J. Mass. Spec. 232:51-57 (2004)).

In certain embodiments, the separation column is a hydrophilic interaction (HILIC) separation column and the glycopeptides are subsequently eluted from the HILIC separation column, for example using a mobile phase gradient to resolve the individual species of glycopeptides, thereby purifying and or separating glycopeptides in the sample. In certain examples, the eluted glycopeptides from the HILIC are separated into one or more fractions. Such fractions can be used for subsequent analysis, such as MS analysis. In certain embodiments, the methods include identifying the glycopeptides and/or glycan present in one or more of the fractions. In certain embodiments, the glycan is an N-glycan. In certain embodiments, the mobile phase gradient is 10 mM ammonium formate, pH 4.5 to 90% ACN with 10 mM ammonium formate, pH 4.5. In certain embodiments, the mobile phase gradient is 0.1% TFA in H$_2$O to be 0.1% TFA in ACN.

The glycopeptide is obtained from glycosylated protein, such as a monoclonal antibody. The glycosylated monoclonal antibody may be prepared by reduction, enzymatic digestion, denaturation, fragmentation, chemical cleavage and a combination thereof. The methods disclosed herein are applicable to any antibody isotype, such as IgG1, IgG2, IgG3, IgG4, or of mixed isotype.

Reduction is to reduce disulfide bonds into two thiols in a 3-dimensional protein, such as monoclonal antibody. Reduction can be performed by heat-denaturing, adding a surfactant, or adding a denaturing agent, e.g., guanidine HCl (6M), in the presence of a reducing agent, e.g. TCEP-HCl. Enzymatic degradation is a digestion of the protein with a protease, e.g., trypsin or *Achromobacter* protease I (Lys-C). In addition, the glycoprotein can be denatured by heat or chemicals, or a combination thereof. Fragmentation involves cleaving protein portions of a single or multi-subunit protein, such as a monoclonal antibody, with physical, biological or chemical methods. For example, an immunoglobulin degrading enzyme from *S. pyogenes* (IdeS) is commonly used for antibody subunit fragmentation.

In various embodiments, an antibody in a sample can be treated and prepared by reduction, enzymatic degradation, denaturation or fragmentation prior to contacting with the hydrophilic enrichment substrate. The methods provide a novel chromatographic method to characterize the glycosylation of proteins, e.g., monoclonal antibody (mAb) therapeutics, by means of fragment, and peptide-level HILIC-UV-MS analyses. In certain embodiments, the samples at any intervening step may be concentrated, desalted or the like.

In some embodiments, the methods further comprise detecting the glycopeptide, for example using the UV signal from the peptide portion of the glycopeptide. This may be done for fractions of a sample and allows the selection of specific fractions for further analysis, for example mass spec (MS) analysis. Thus, in further embodiments, the detection step comprises mass spectroscopy or liquid chromatography-mass spectroscopy (LC-MS). In application of mass spectrometry for the analysis of biomolecules, the molecules are transferred from the liquid or solid phases to gas phase and to vacuum phase. Since many biomolecules are both large and fragile (proteins being a prime example), two of the most effective methods for their transfer to the vacuum phase are matrix-assisted laser desorption ionization (MALDI) or electrospray ionization (ESI). Aspects of the use of these methods, and sample preparation requirements, are known to those of ordinary skill in the art. In general, ESI is more sensitive, while MALDI is faster. Significantly, some peptides ionize better in MALDI mode than ESI, and vice versa (Genome Technology, June 220, p 52). The extraction channel methods and devices of the instant invention are particularly suited to preparing samples for MS analysis, especially biomolecule samples such as glycopeptides. An important advantage of the invention is that it allows for the preparation of an enriched sample that can be directly analyzed, without the need for intervening process steps, e.g., concentration or desalting.

ESI is performed by mixing the sample with volatile acid and organic solvent and infusing it through a conductive needle charged with high voltage. The charged droplets that are sprayed (or ejected) from the needle end are directed into the mass spectrometer, and are dried up by heat and vacuum as they fly in. After the drops dry, the remaining charged molecules are directed by electromagnetic lenses into the mass detector and mass analyzed. In one embodiment, the eluted sample is deposited directly from the capillary into an electrospray nozzle, e.g., the capillary functions as the sample loader. In another embodiment, the capillary itself functions as both the extraction device and the electrospray nozzle.

For MALDI, the analyte molecules (e.g., proteins) are deposited on metal targets and co-crystallized with an organic matrix. The samples are dried and inserted into the mass spectrometer, and typically analyzed via time-of-flight (TOF) detection. In one embodiment, the eluted sample is deposited directly from the capillary onto the metal target, e.g., the capillary itself functions as the sample loader. In one embodiment, the extracted analyte is deposited on a MALDI target, a MALDI ionization matrix is added, and the sample is ionized and analyzed, e.g., by TOF detection.

In some embodiments, other ionization modes are used e.g. ESI-MS, turbospray ionization mass spectrometry, nanospray ionization mass spectrometry, thermospray ionization mass spectrometry, sonic spray ionization mass spectrometry, SELDI-MS and MALDI-MS. In general, an advantage of these methods is that they allow for the "just-in-time" purification of sample and direct introduction into the ionizing environment. It is important to note that the various ionization and detection modes introduce their own constraints on the nature of the desorption solution used, and it is important that the desorption solution be compatible with both. For example, the sample matrix in many applications must have low ionic strength, or reside within a particular pH range, etc. In ESI, salt in the sample can prevent detection by lowering the ionization or by clogging the nozzle. This problem is addressed by presenting the analyte in low salt and/or by the use of a volatile salt. In the case of MALDI, the analyte should be in a solvent compatible with spotting on the target and with the ionization matrix employed.

EXAMPLES

The following examples are put forth so as to provide those of ordinary skill in the art with a complete disclosure and description of how to make and use the methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Comparison of Previous Methods Based on RPLC-UV-MS of Glycopeptides and Released Glycan.

Figure 3:
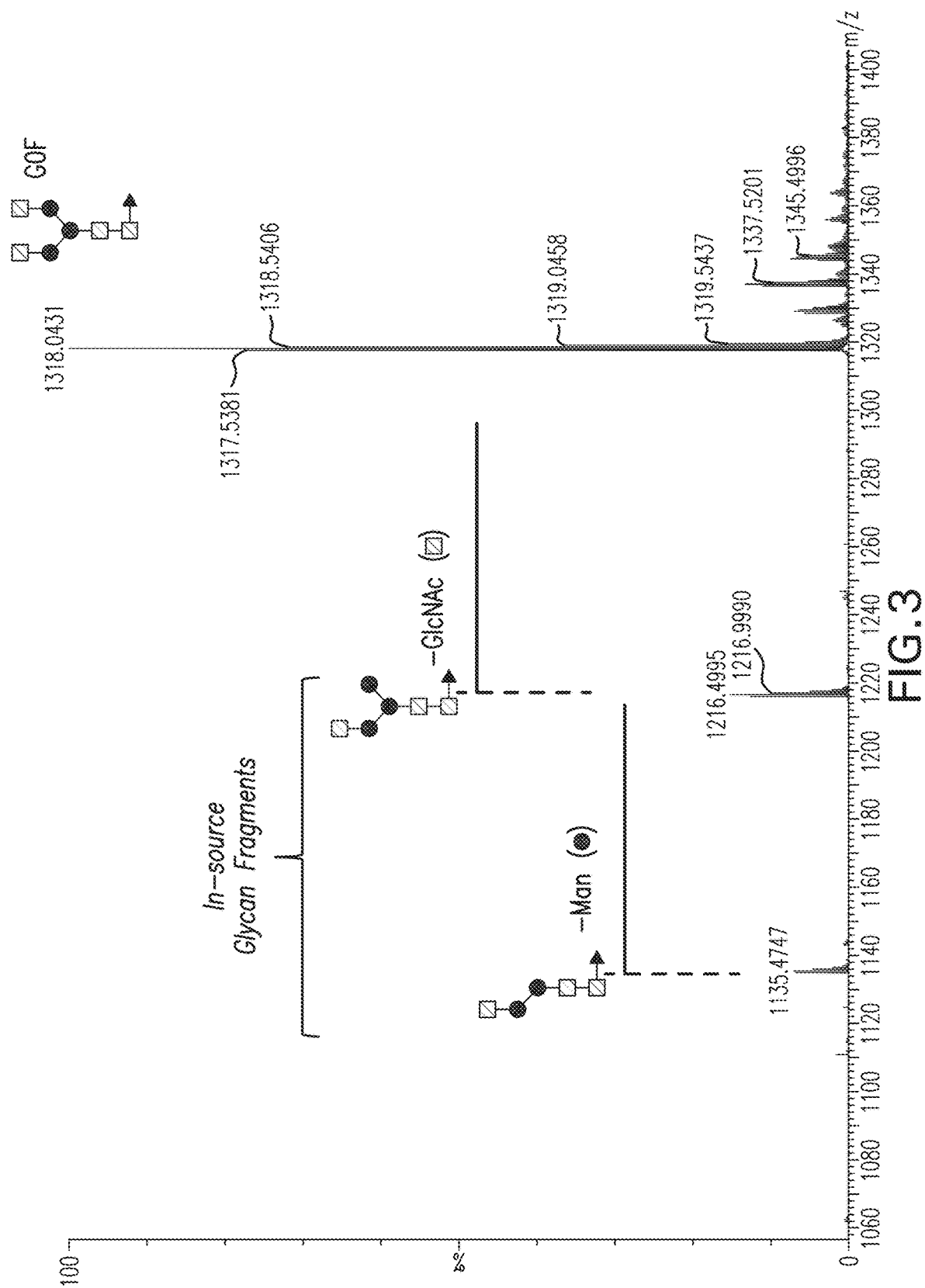
FIG. 3 shows a mass spectra demonstrating that discrepancies between glycoform quantitations by glycopeptide and released glycan methods (see FIG. 2) are likely due to in-source fragmentation of the sugar backbone by MS in glycopeptide analysis, causing an increase of truncated glycan artifacts (i.e., G0F-GlcNAc and G1F-GlcNAc) and a decrease of the main glycan (i.e., G0F and G1F). The released glycan method quantifies glycoforms by fluorescence of label bound to the released glycan, not by MS signal.
Figure 4:
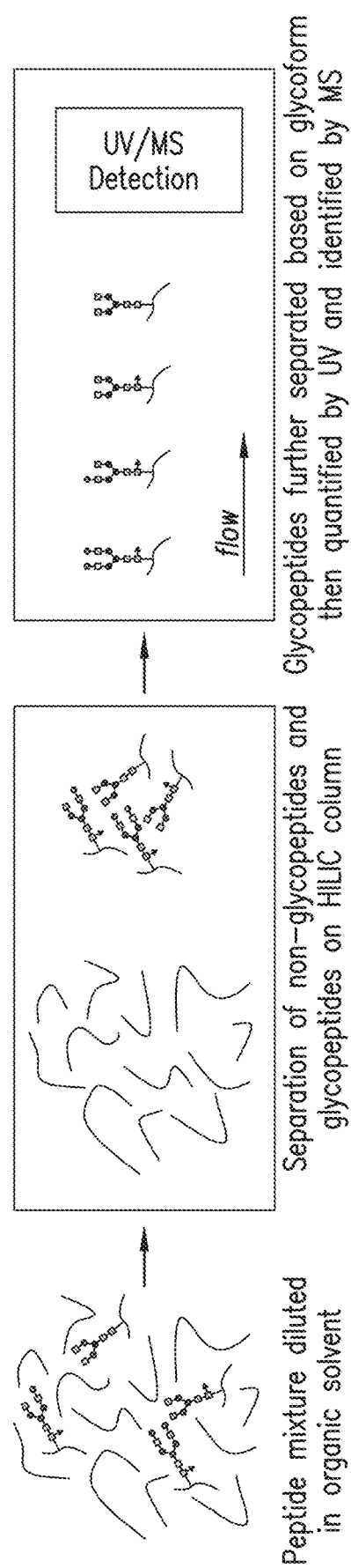
FIG. 4 shows a work-flow diagram for methods of glycopeptide quantitation as disclosed herein.

FIG. 1 is schematic work-flow diagram illustrating current methods of glycopeptide quantitation. The therapeutic antibody was digested with trypsin after being denatured, reduced and alkylated. Relative quantitation was done by peak intensity (height) of glycopeptide mass peaks. The released glycan method quantifies glycoforms by fluorescence of label bound to the released glycan, not by MS signal. FIG. 2 is a table showing a comparison of relative quantitation of each glycoform quantified by released glycans (labeled with a fluorescent reagent, RapiFluor-MS from Waters) and glycopeptides. Major differences in quantitations between methods are shown in rows 3, 5, 7 and 8. FIG. 3 is a mass spectra demonstrating that discrepancies between glycoform quantitations by glycopeptide and released glycan methods are likely due to in-source fragmentation of the sugar backbone by MS in glycopeptide analysis, causing an increase of truncated glycan artifacts (i.e. G0F-GlcNAc and G1F-GlcNAc) and a decrease of the main glycan (i.e. G0F and G1F). This result demonstrates that new and improved methods are needed for glycan analysis at the peptide level.

Example 2: New Methods of Glycopeptide Analysis Using HILIC-UV-MS.

Peptides from therapeutic antibodies were prepared by either reduced or non-reduced peptide mapping methods routinely performed. Digests were then diluted to 80% ACN final (v/v) prior to HILIC-UV-MS analysis.

Figure 5:
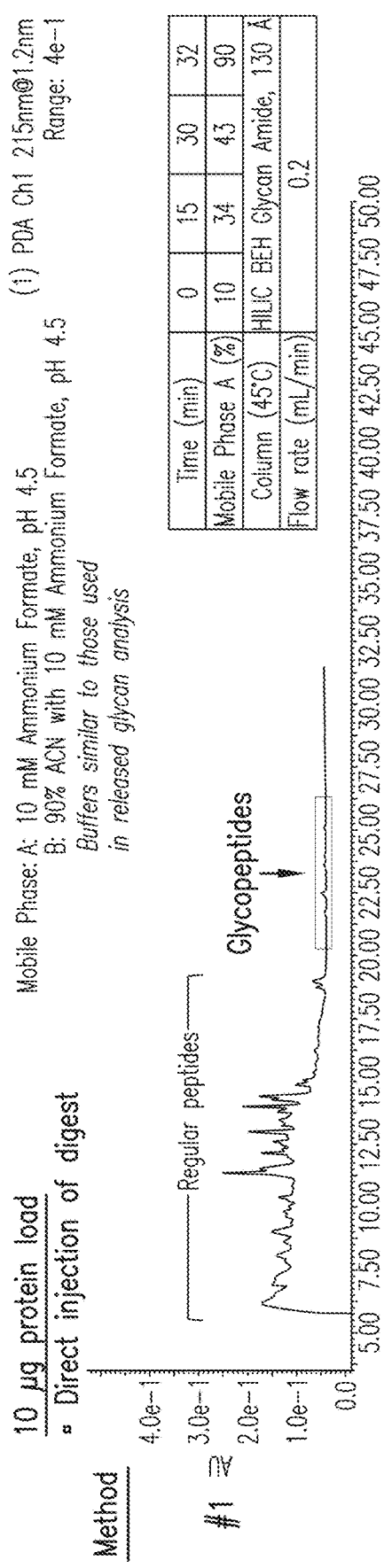
FIG. 5 shows a set of HILIC-UV chromatograms of mAb1 peptides showing the results of a separation of mAb1 peptides obtained from tryptic digest by two different methods.
Figure 5:
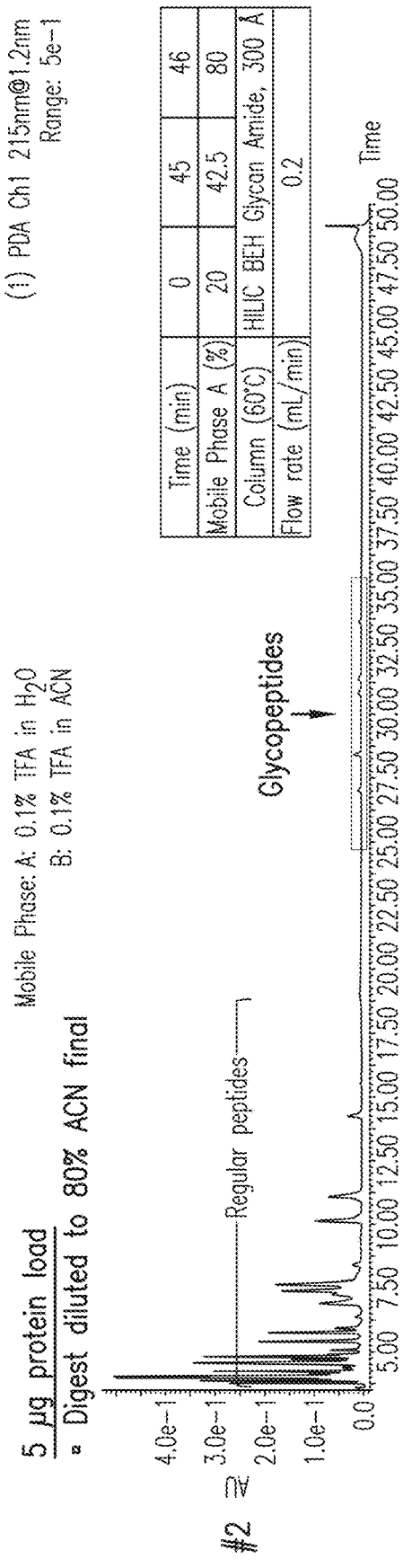
Figure 6:
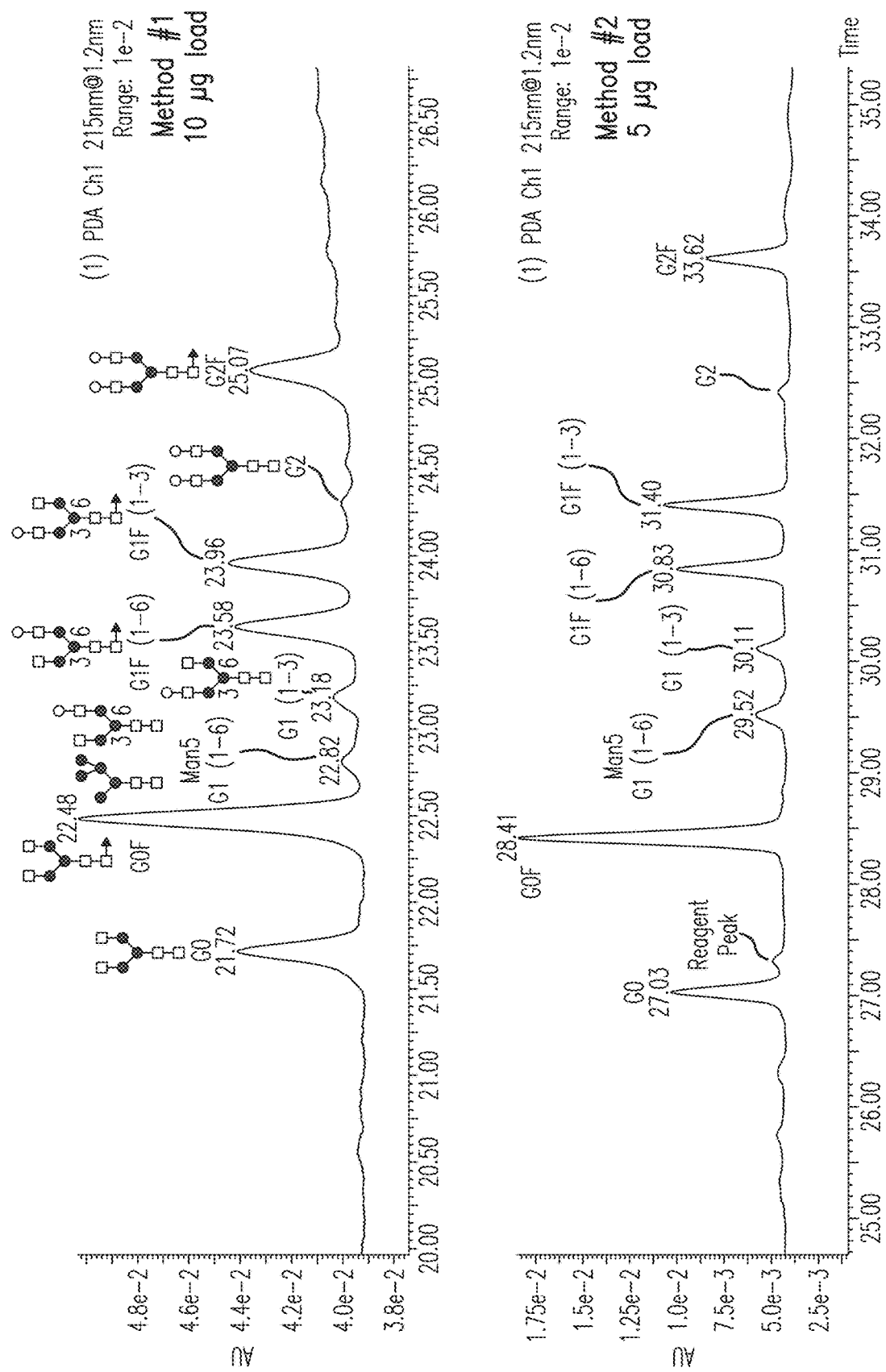
FIG. 6 shows a close up of the glycopeptide portion of the trace shown in FIG. 5 demonstrating that method #2 had better separation, sharper peaks, and greater S/N ratio.
Figure 7:
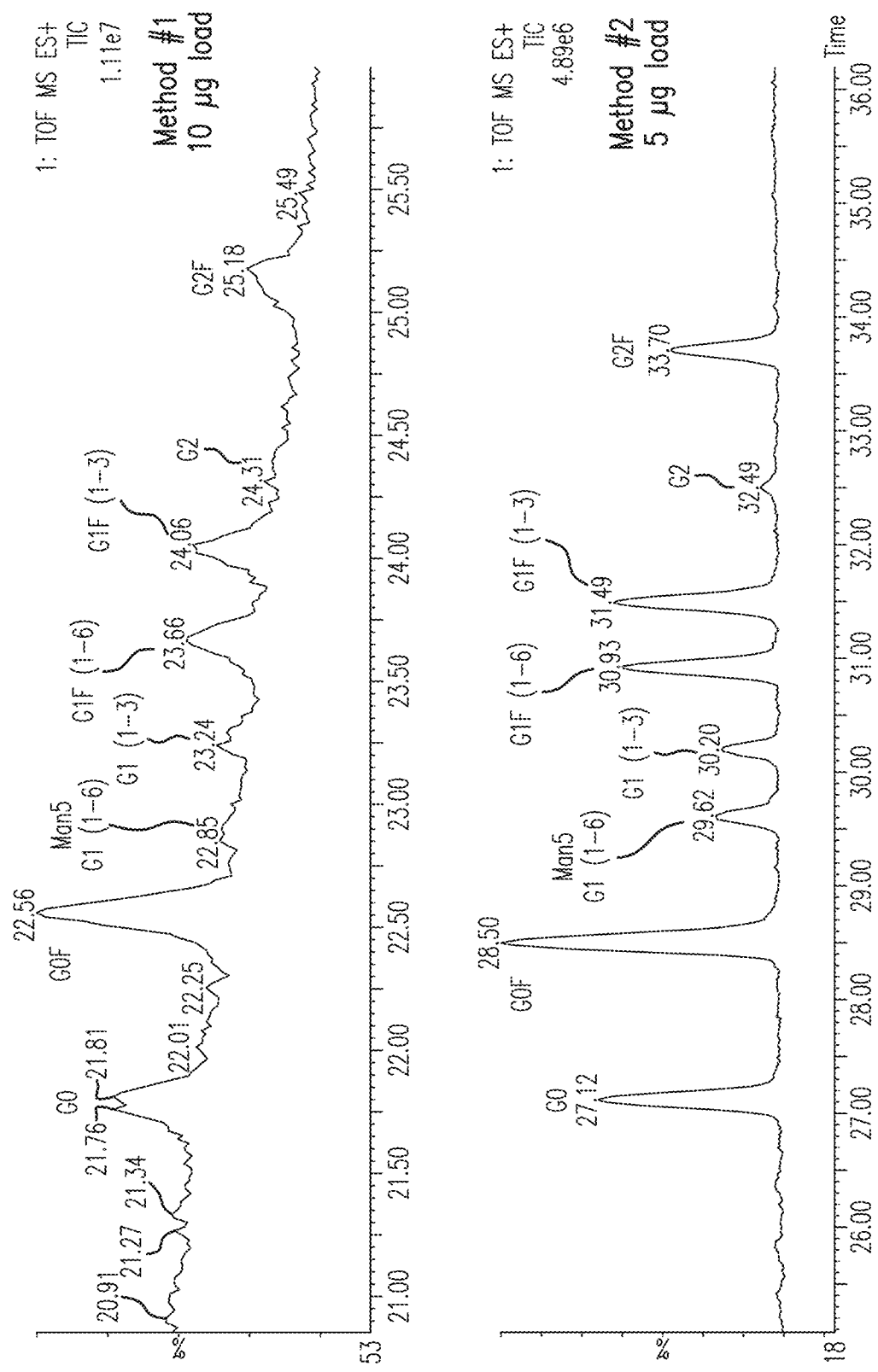
FIG. 7 shows a set of HILIC-TIC chromatograms of mAb1 glycopeptides zooming-in on the glycopeptides. As shown, Method #2 had greater S/N ratio of MS signal.
Figure 8A:
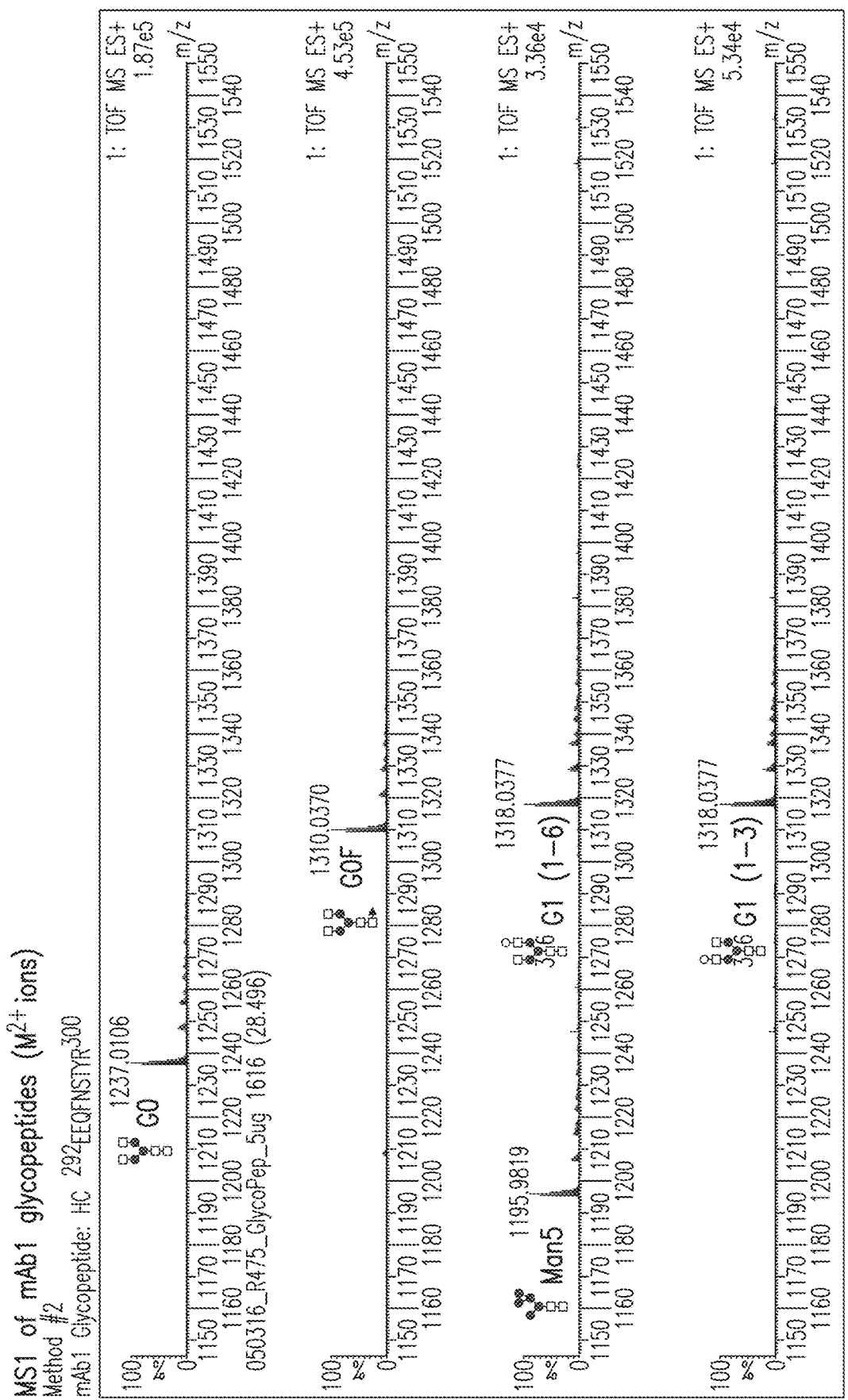
FIGS. 8A and 8B show MS1 spectra of mAb1 glycopeptides ($M^{2+}$ ions).
Figure 8B:
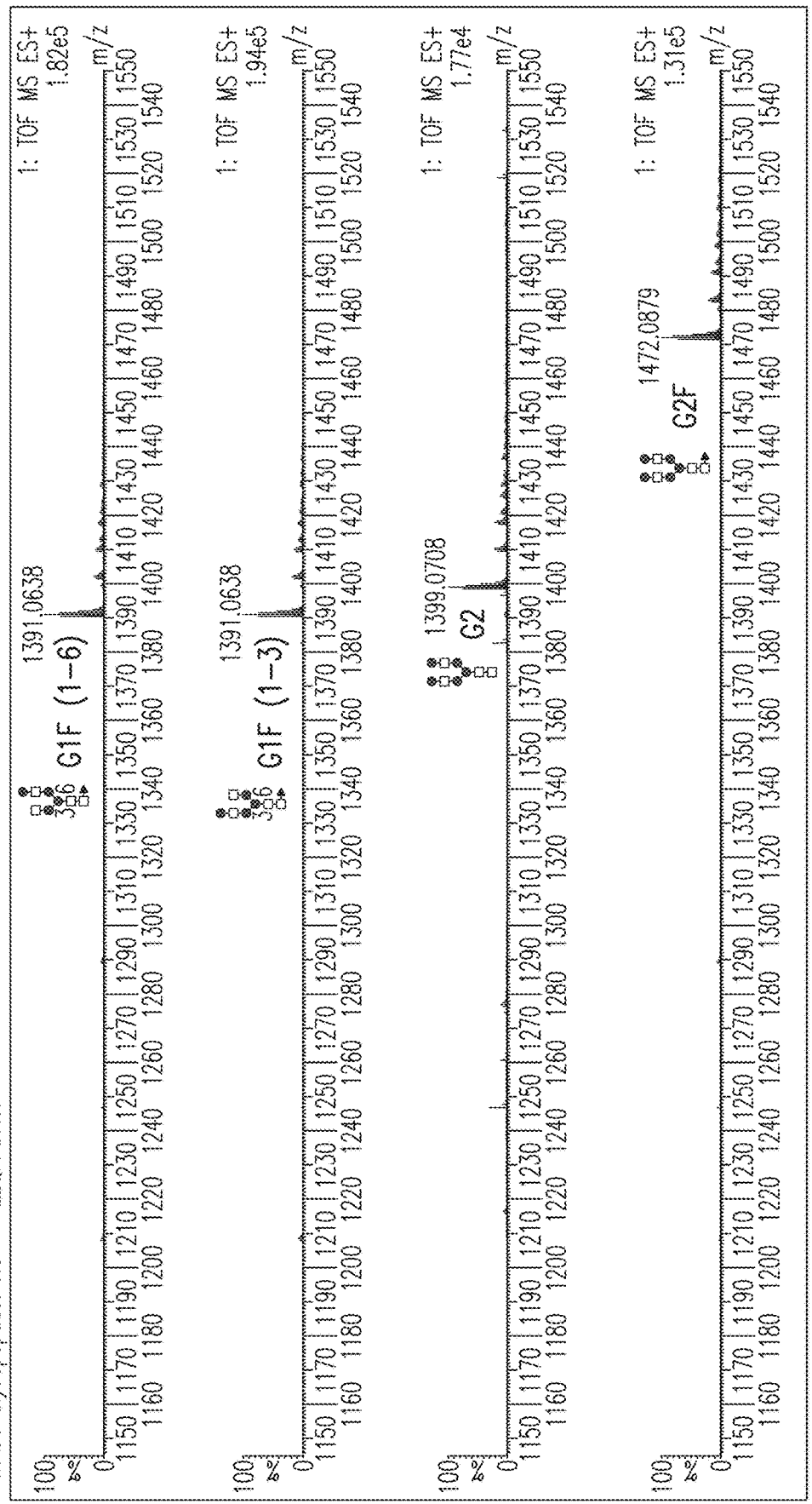
Figure 9:
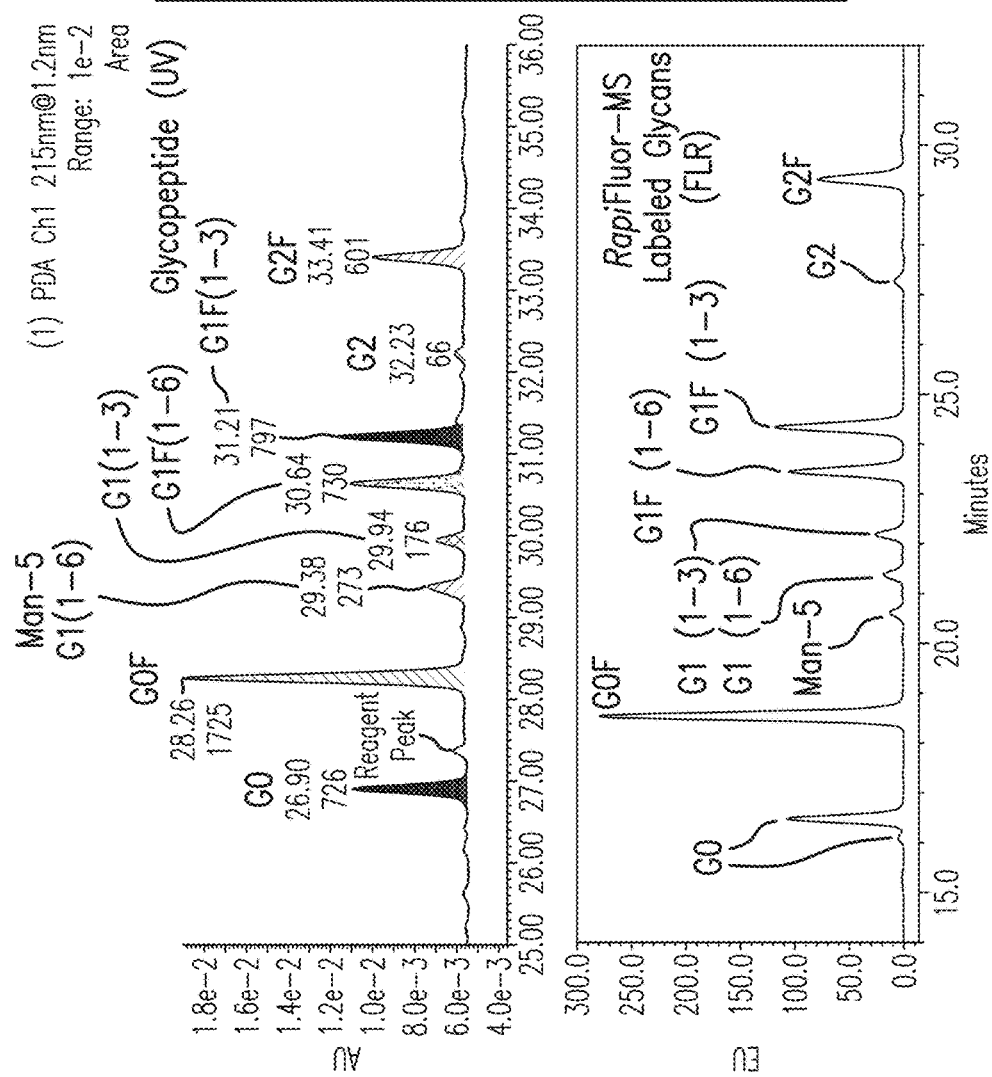
FIG. 9 shows a set of traces and a table showing a comparison of glycoform quantitation by glycopeptide separation on a HILIC column with released glycan analysis.

LC System: Waters ACQUITY I-Class UPLC® System with PDA (UV) Detector
MS System: Waters XEVO G2-S QTof or Thermo Scientific Q Exactive Plus
Column: Waters ACQUITY UPLC® Glycan BEH Amide HILIC Column FIG. 5 is a set of HILIC-UV chromatograms of mAb1 peptides showing the results of a separation of mAb1 peptides obtained from tryptic digest by two different methods. Method #1 uses ammonium formate while method #2 uses TFA. The relative levels of different glycoforms were quantified by UV using PDA detector with online MS detection. FIG. 6 is a close up of the glycopeptide portion of the trace shown in FIG. 5 demonstrating that method #2 had better separation, sharper peaks, and greater S/N ratio. FIG. 7 is a set of HILIC-TIC chromatograms of mAb1 glycopeptides zooming-in on the glycopeptide portion. As shown, Method #2 had greater S/N ratio of MS signal. FIGS. 8A and 8B are MS1 spectra of mAb1 glycopeptides ($M^{2+}$ ions). MS in-source fragmentation of glycans was not a factor in glycoform quantitation by UV. FIG. 9 is a set of traces and a table showing a comparison of glycopeptide separation on a HILIC column with released glycan analysis. Similar glycoform quantitations by glycopeptide and released glycan analyses were observed for mAb1. Importantly, no major differences in glycoform quantitations between the two methods were observed, demonstrating that HILIC column separation was viable for glycopeptide analysis. In addition, total fucosylation and galactosylation levels were consistent between the two analyses. Truncated glycan artifacts do not impact the glycopeptide quantitation by HILIC-UV. This suggests that the artifacts observed by previous RPLC analysis were due to in-source fragmentation of glycans induced by MS.

Figure 10:
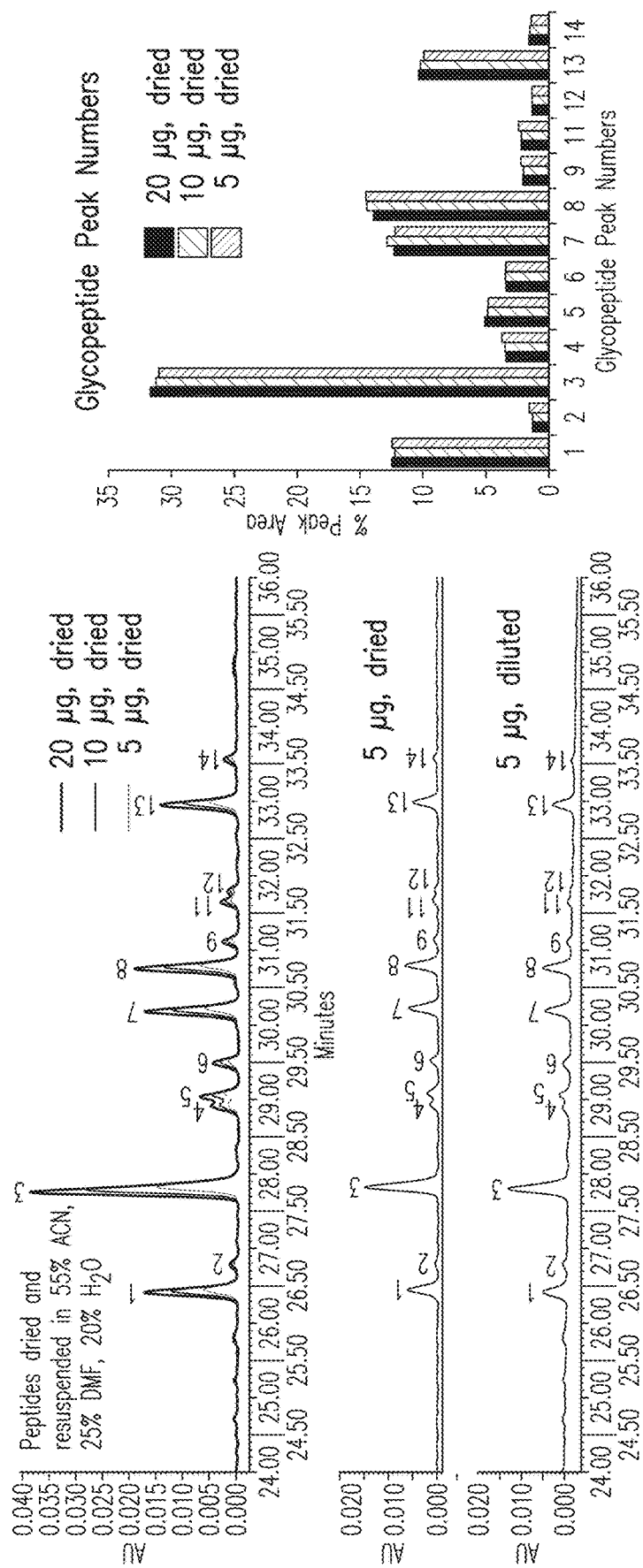
FIG. 10 shows a set of traces and a table demonstrating that drying peptide digests could help to concentrate glycopeptides but did not affect the UV signal and relative % PA of glycans.
Figure 11:
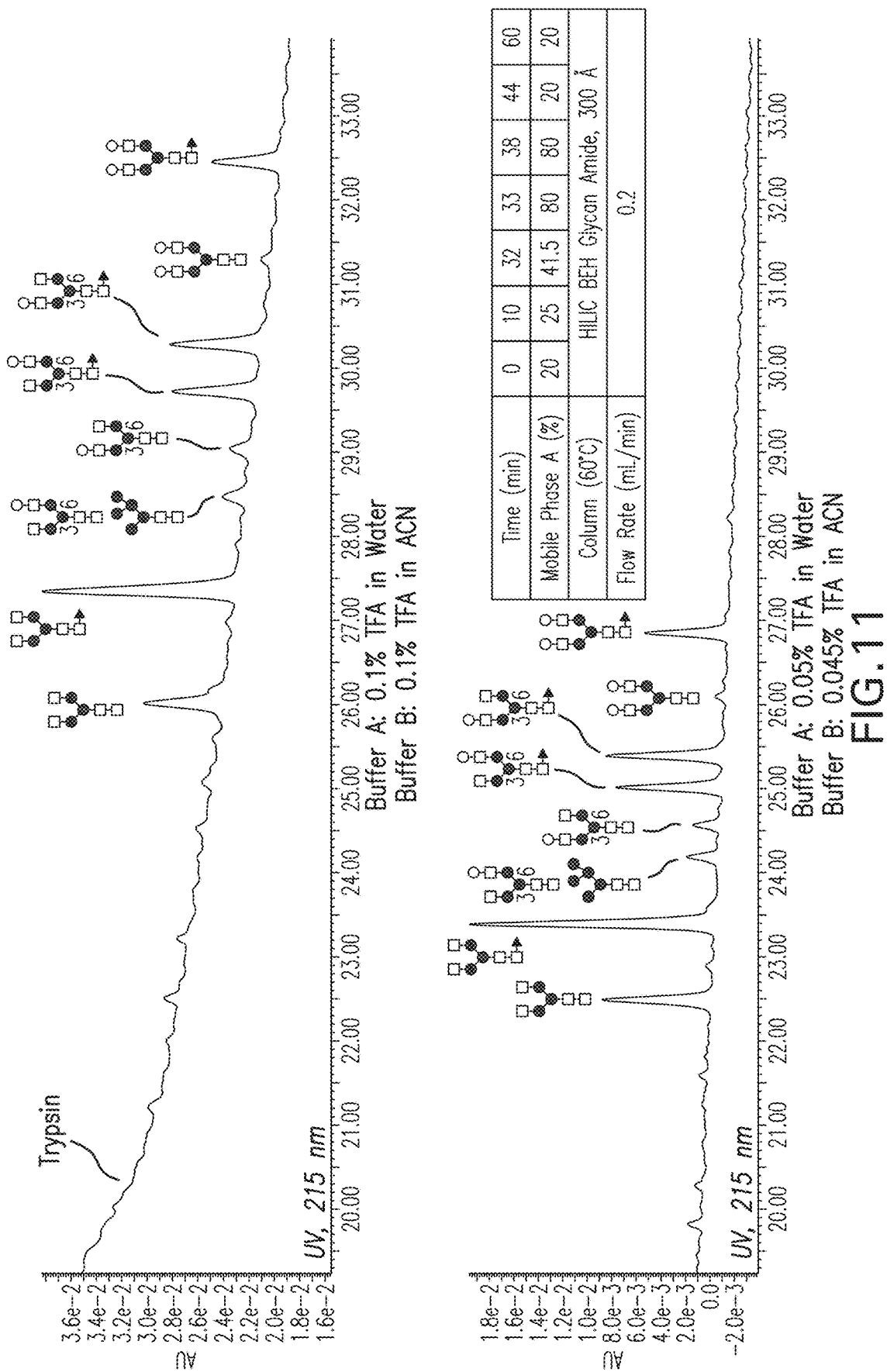
FIG. 11 shows a set of traces illustrating that changes made to simplify mobile phase preparations and improve peak integration by using 0.05% and 0.045% TFA in water and ACN, respectively (RP-LC peptide mapping mobile phase).
Figure 12A:
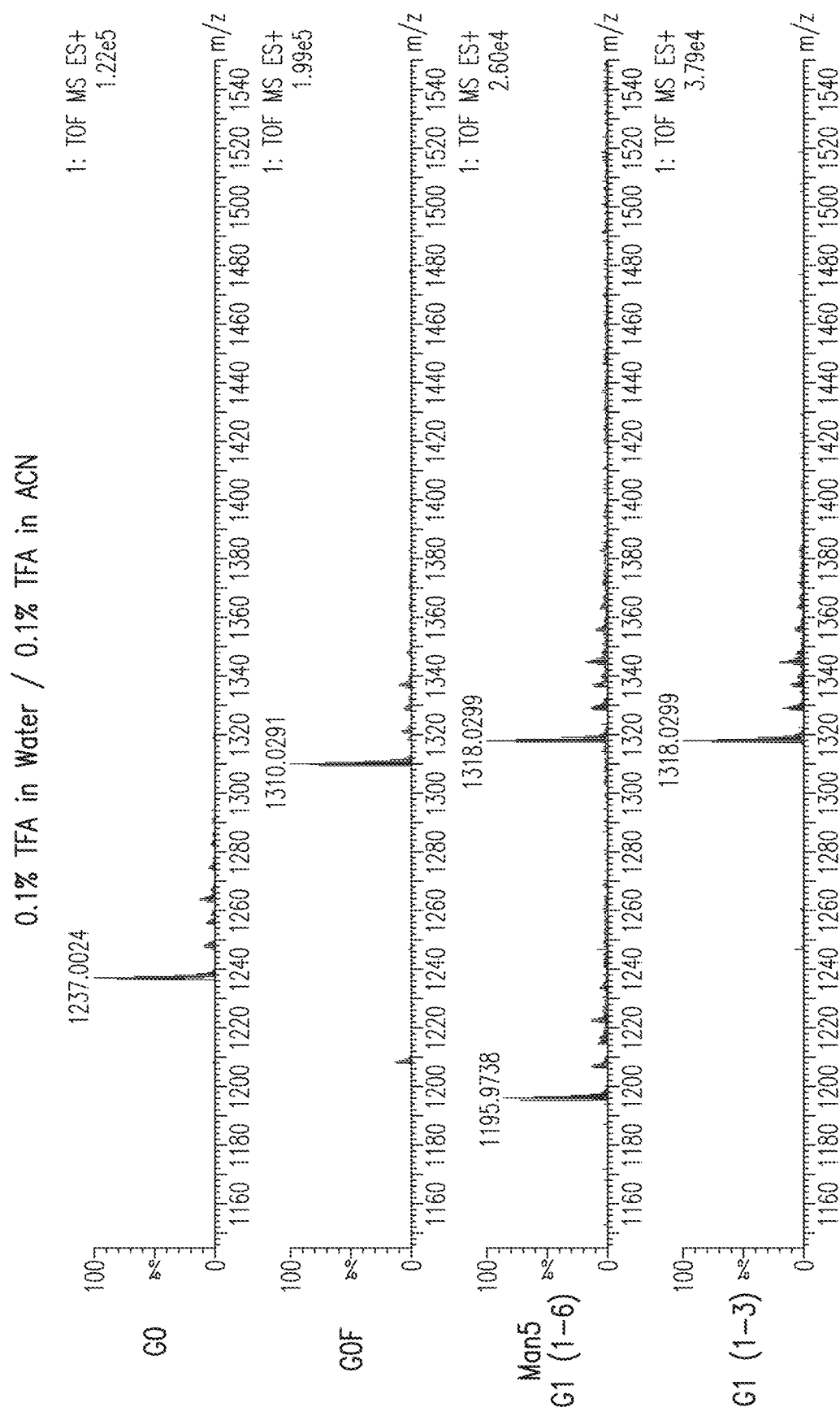
FIGS. 12A, 12B, 12C and 12D show a set of mass spectra results demonstrating that mobile phase change had no impact on MS signal of glycopeptides ($M^{2+}$ ions).
Figure 12B:
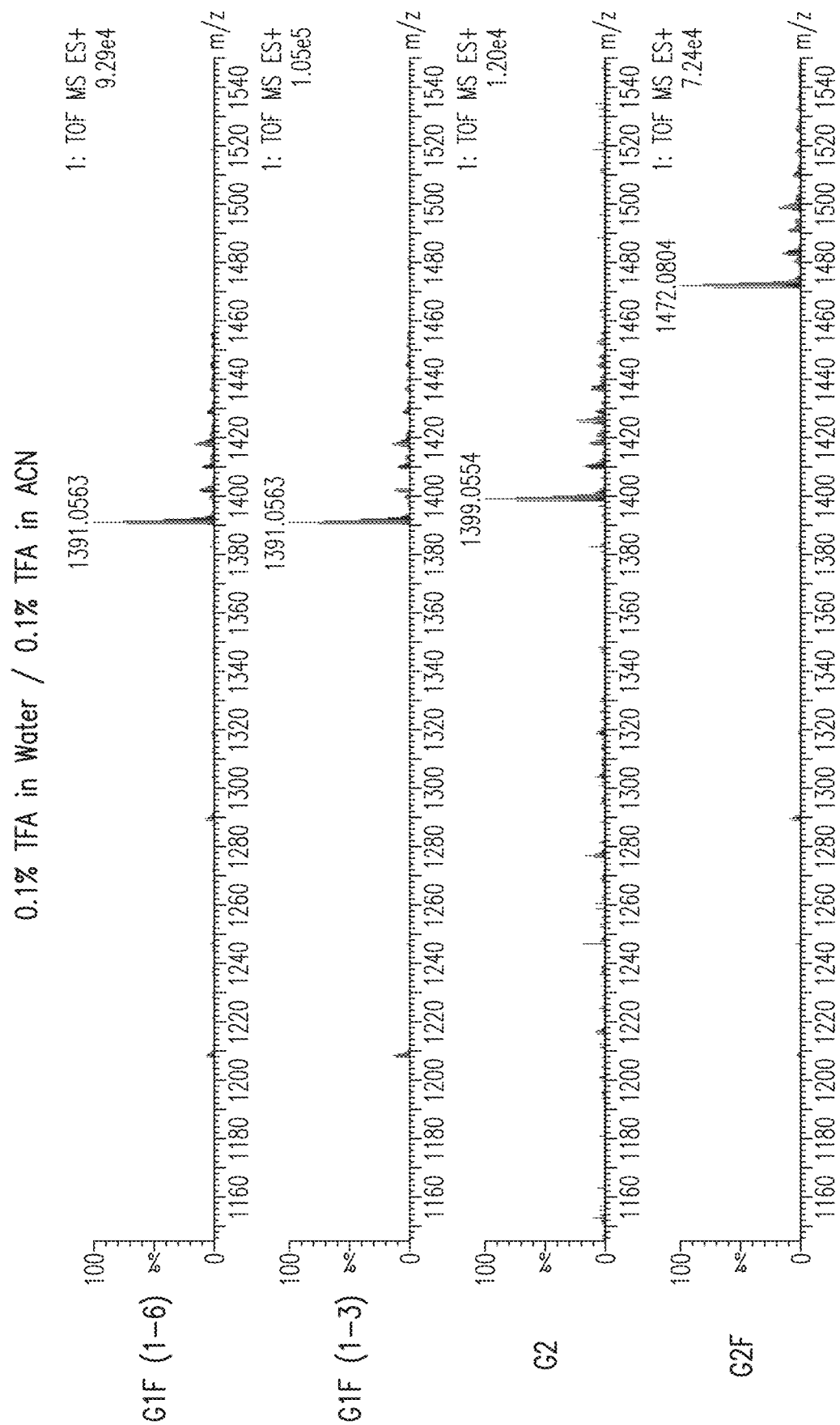
Figure 12C:
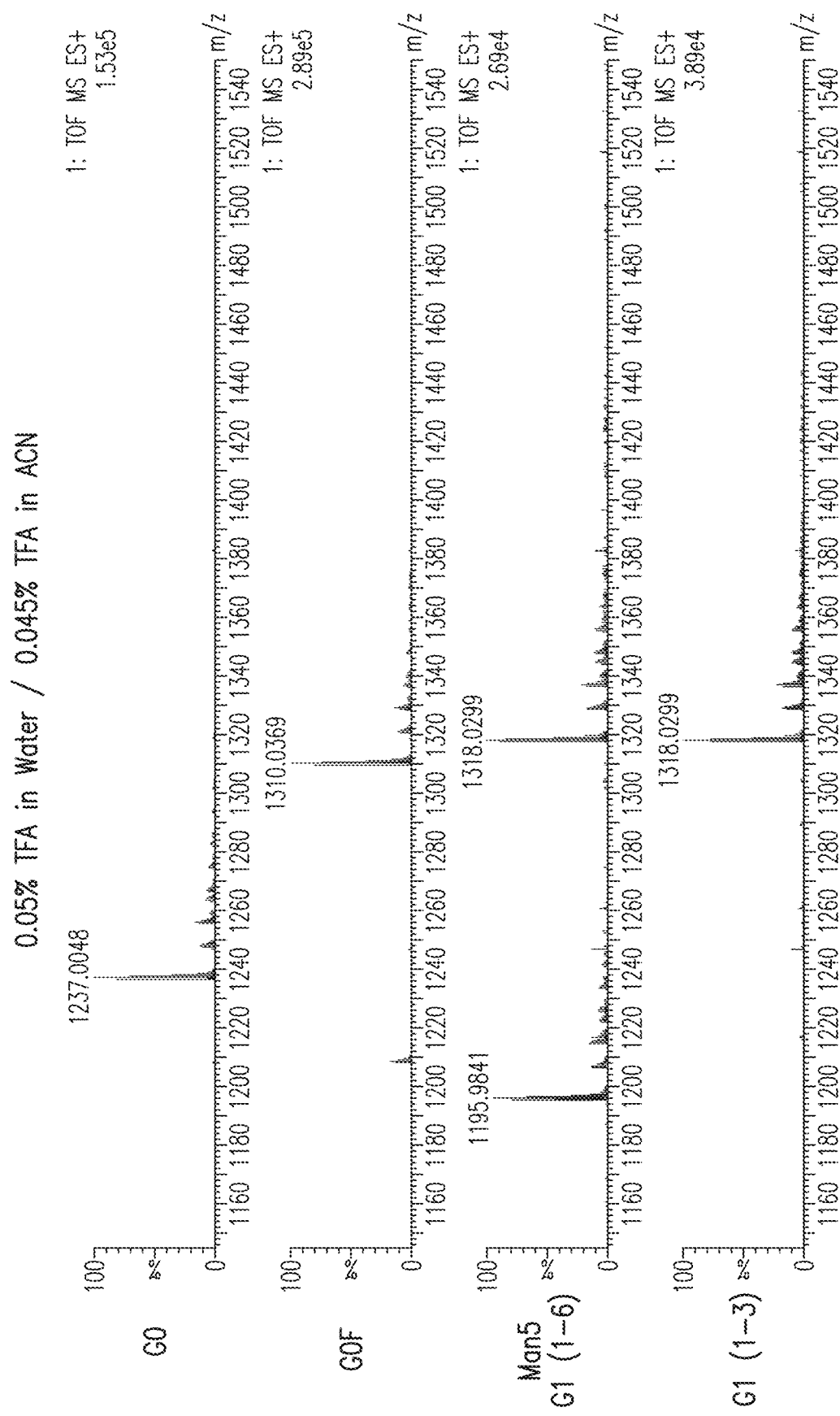
Figure 12D:
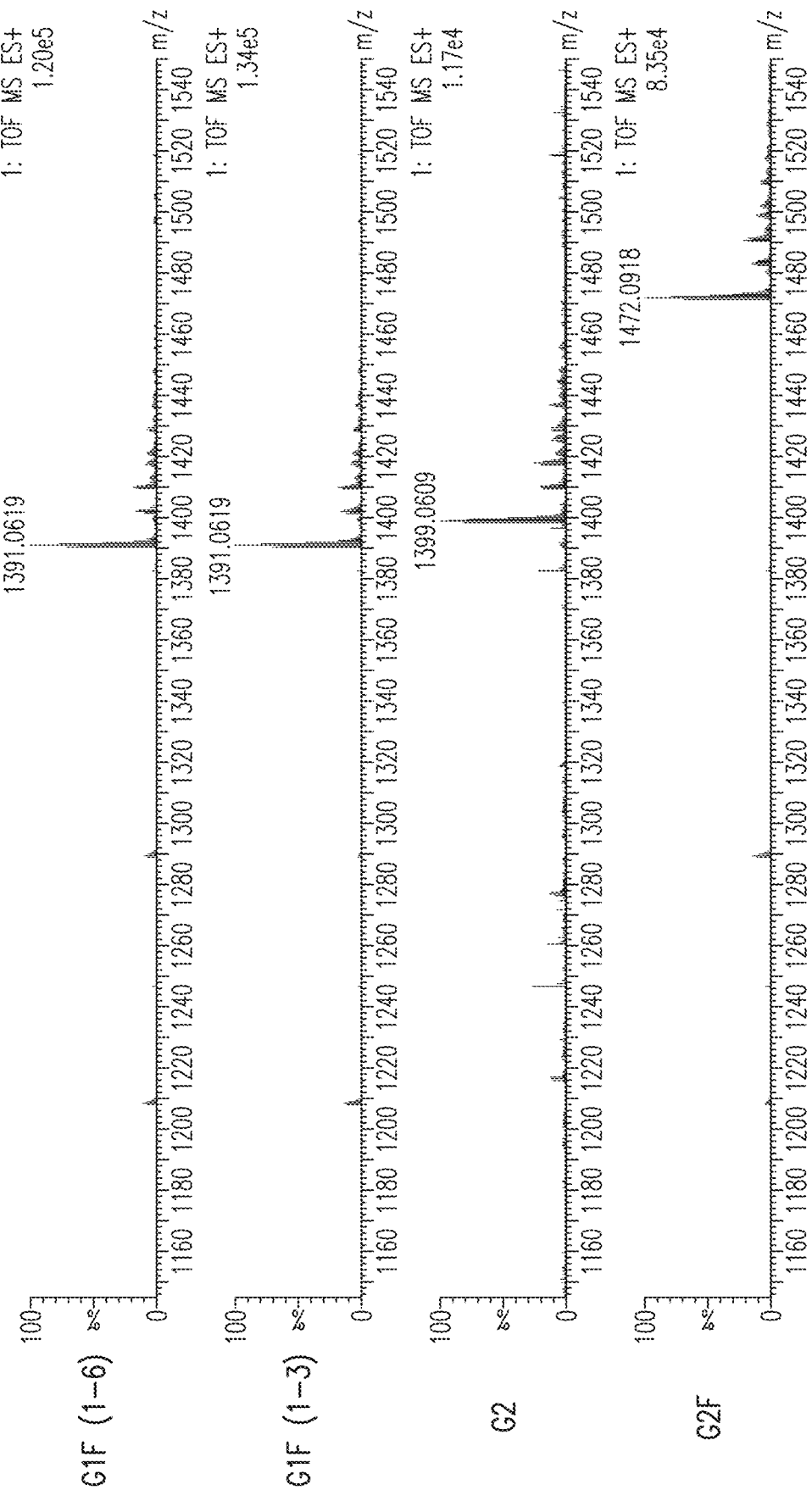
Figure 13:
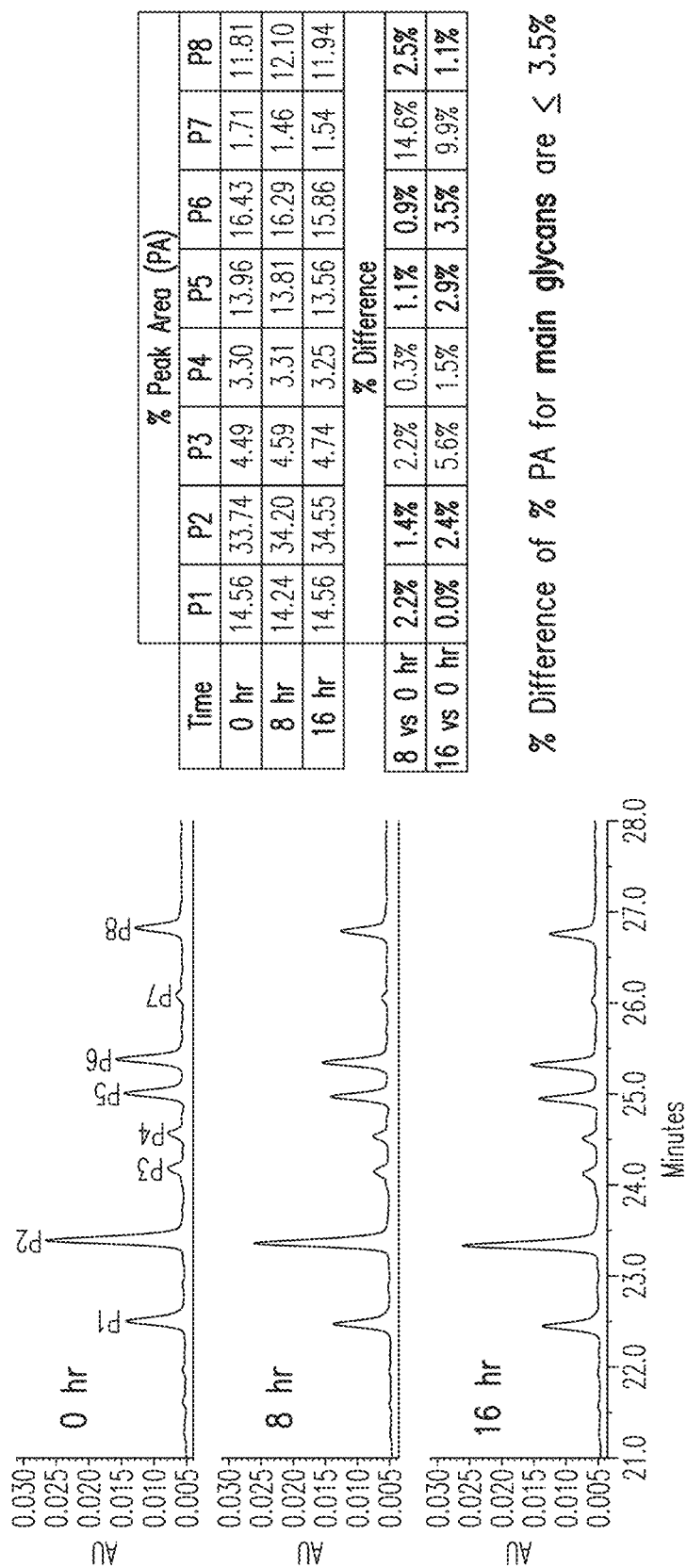
FIG. 13 shows a set of traces demonstrating the solution stability of mAb1 glycopeptides diluted to 80% ACN.

Dilute Digests can be Concentrated with Drying: If a digest has a concentration of <0.5 mg/mL, the sample may be concentrated by vacuum drying and resuspending the dried peptides in 80:20 ACN:Water (v/v) with 0.2% TFA to 0.5 mg/mL or above. Low pH is required to maintain peptide solubility in highly organic solvent. FIG. 10 is a set of traces and a table demonstrating that drying peptides helped to concentrate the peptides and is consistent using different sample amounts (e.g. 5-20 μg, left top), but did not affect UV signal (left bottom) and relative % PA (right table) of glycans. FIG. 11 is a set of traces showing changes made to simplify mobile phase preparations and improve peak integration. Mobile phase changed from 0.1% TFA in water/ACN to the same mobile phase buffers used for peptide mapping (0.05% and 0.045% TFA in water and ACN, respectively). FIGS. 12A, 12B, 12C and 12D are a set of mass spectra results showing that mobile phase change had no impact on MS signal of glycopeptides ($M^{2+}$ ions). FIG. 13 is a set of traces demonstrating the solution stability of mAb1 glycopeptides diluted into 80% ACN.

Figure 14:
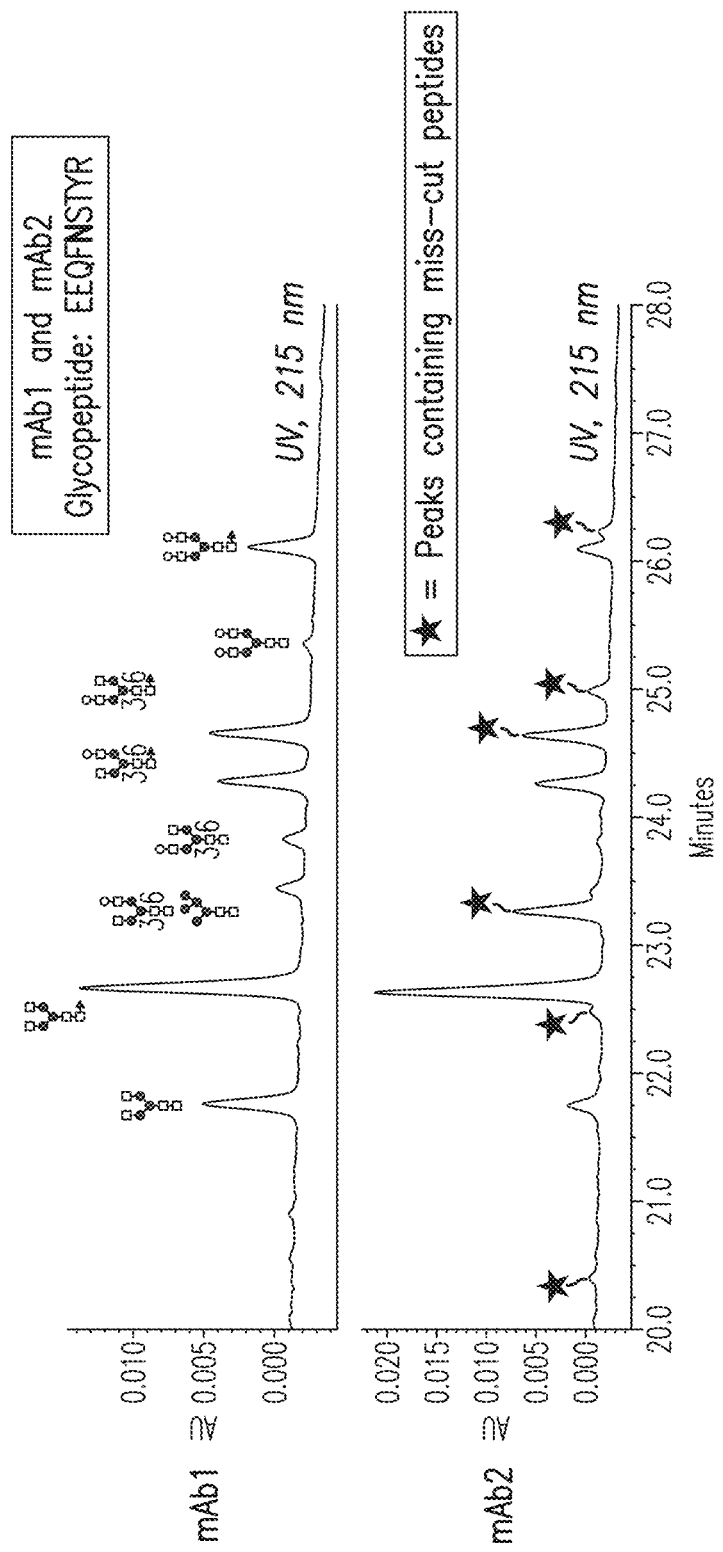
FIG. 14 shows a set of traces demonstrating that tryptic digests with miss-cut glycopeptides complicate quantitation of glycopeptides by UV.
Figure 15:
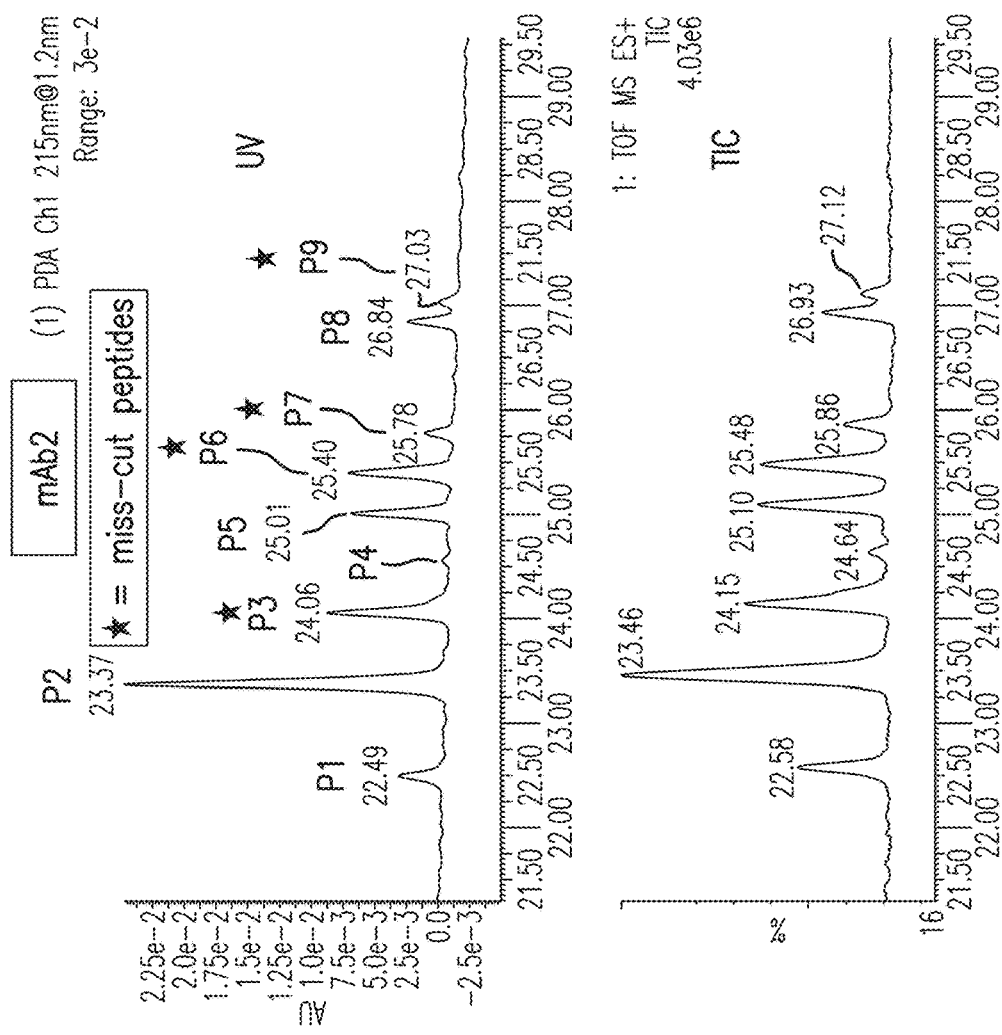
FIG. 15 shows a set of traces and a table demonstrating that with online MS data EIC can be used to find the percentage of miss-cut glycopeptides in each peak to help for glycoform quantitation.

Identification of Miss-cut Glycopeptides: FIG. 14 is a set of traces showing that digests with miss-cut glycopeptides complicate quantitation of glycopeptides by UV. FIG. 15 is a set of traces and a table demonstrating that with online MS data Extraction ion chromatography (EIC) can be used to find the percentage of miss-cut glycopeptides in each peak. EIC from online MS detection was used to calculate the ratio of miss-cut peptide(s) to regular tryptic glycopeptide(s) in each co-eluting peak and to filter out the UV signal due to miss-cuts for glycoform quantitation. Alternatively, the digest can be re-digested with trypsin to convert miss-cuts into regular tryptic glycopeptides.

Figure 16:
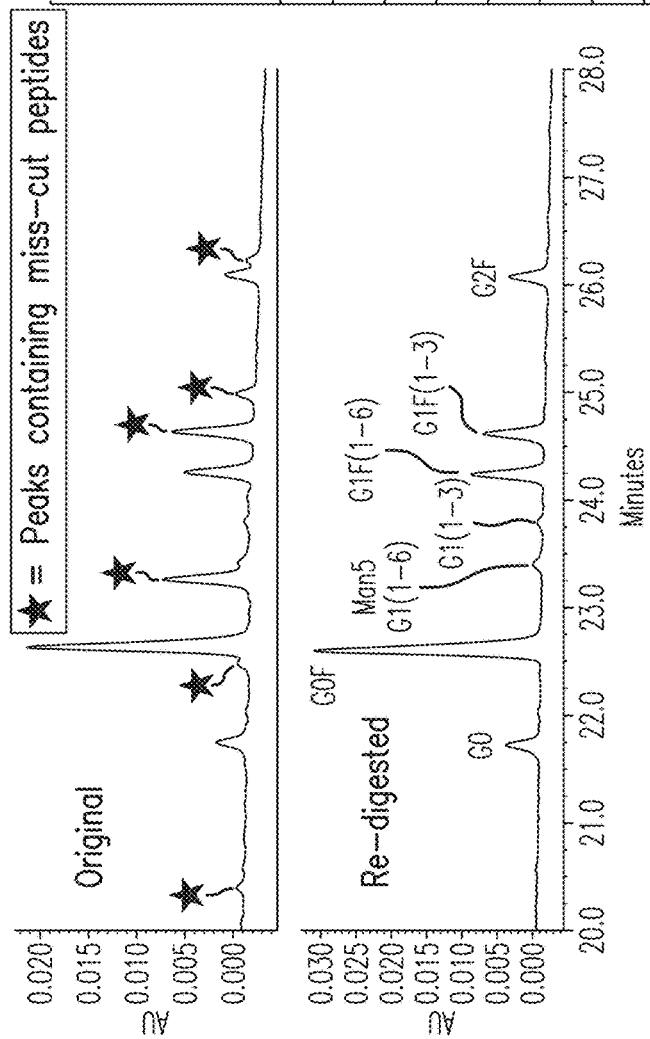
FIG. 16 shows a set of traces and a table demonstrating that re-digestion of mAb2 with trypsin removed miss-cut glycopeptides to help for glycoform quantitation.

For re-digestion, the following protocol was used: Raise pH of digest to ~8.0 with 3 M Tris base; Add 1:5 E:S ratio (w/w) of trypsin, incubate at 50° C. for 1 hour; and Add 0.2% TFA (final) and dilute to 80% ACN (final) for HILIC analysis. FIG. 16 is a set of traces and a table demonstrating that re-digestion of mAb2 with trypsin removed miss-cut glycopeptide interference for glycoform quantitation.

Reagent Contaminated Digests can be Cleaned-up with Solid Phase Extraction and Concentrated with Drying: If a digest has a concentration of <0.5 mg/mL, it may be concentrated by vacuum drying and resuspending the dried peptides in 80:20 ACN:Water (v/v) with 0.2% TFA to 0.5 mg/mL or above. Low pH is required to maintain peptide solubility in highly organic solvent.

The digest can be cleaned from salts, reagents, or detergents by solid phase extraction (SPE) and then vacuum dried.

Waters GlycoWorks HILIC µElution Plate (Part No. 186002780): Wash with water, then 80:15 ACN:Water (v/v); Add peptide digest (diluted to 80% ACN, v/v); Wash twice with 1:9:90 Formic Acid:Water:ACN (v/v); Elute with 200 mM Ammonium Formate, 5% ACN; Vacuum dry eluted glycopeptides; and Resuspend in 80:20 ACN:Water (v/v) with 0.2% TFA to 0.5 mg/mL.

Figure 17:
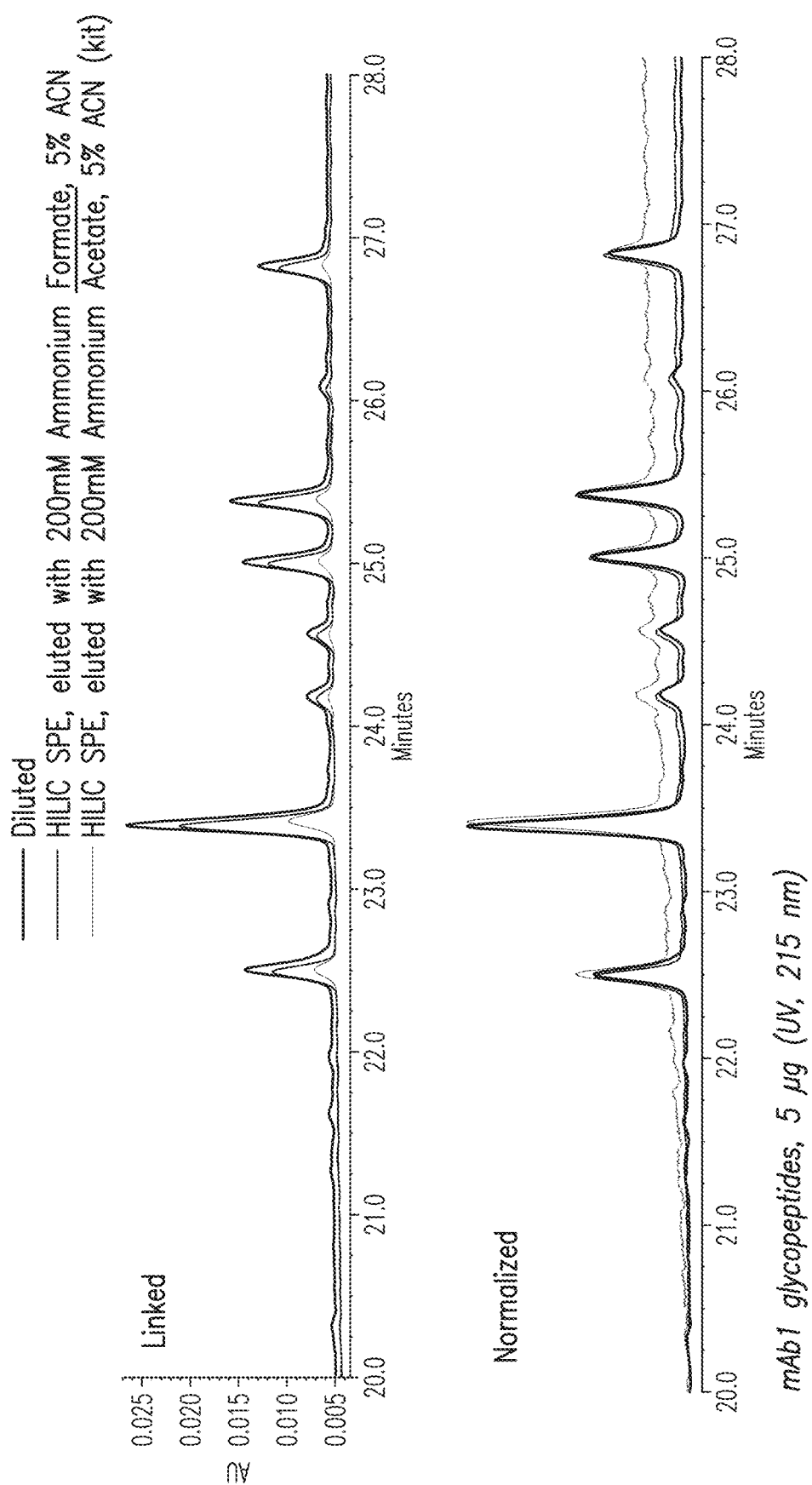
FIG. 17 shows a set of traces demonstrating that ammonium formate significantly improved the elution of glycopeptides from HILIC SPE.

FIG. 17 is a set of traces demonstrating that ammonium formate significantly improves the elution of glycopeptides from HILIC SPE.

Figure 18:
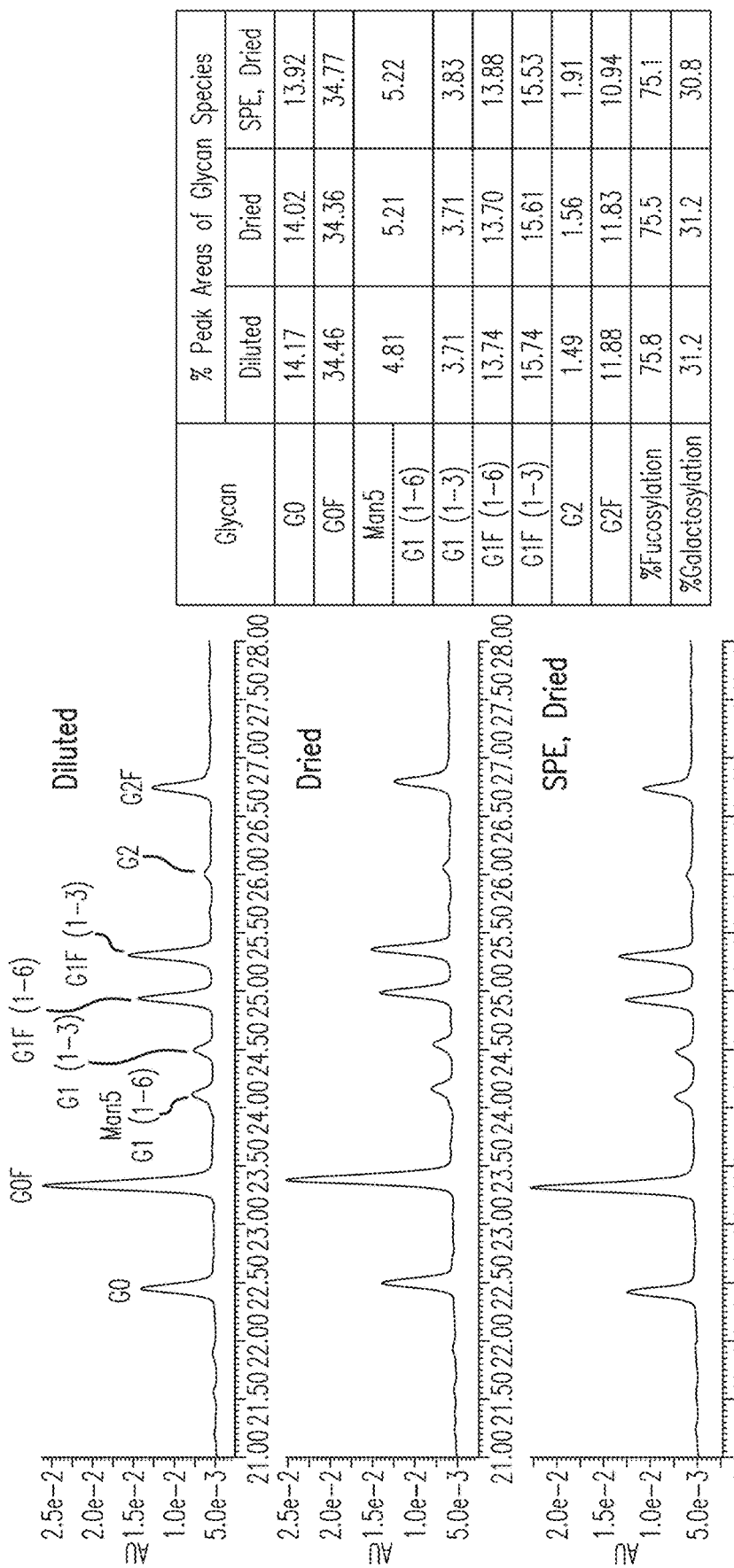
FIG. 18 shows a set of traces and a table demonstrating that drying or SPE clean-up/drying had no effect on mAb1 glycopeptide quantitation.

FIG. 18 is a set of traces and a table demonstrating that drying or SPE clean-up/drying has no affect on mAb1 glycopeptide quantitation.

Figure 19:
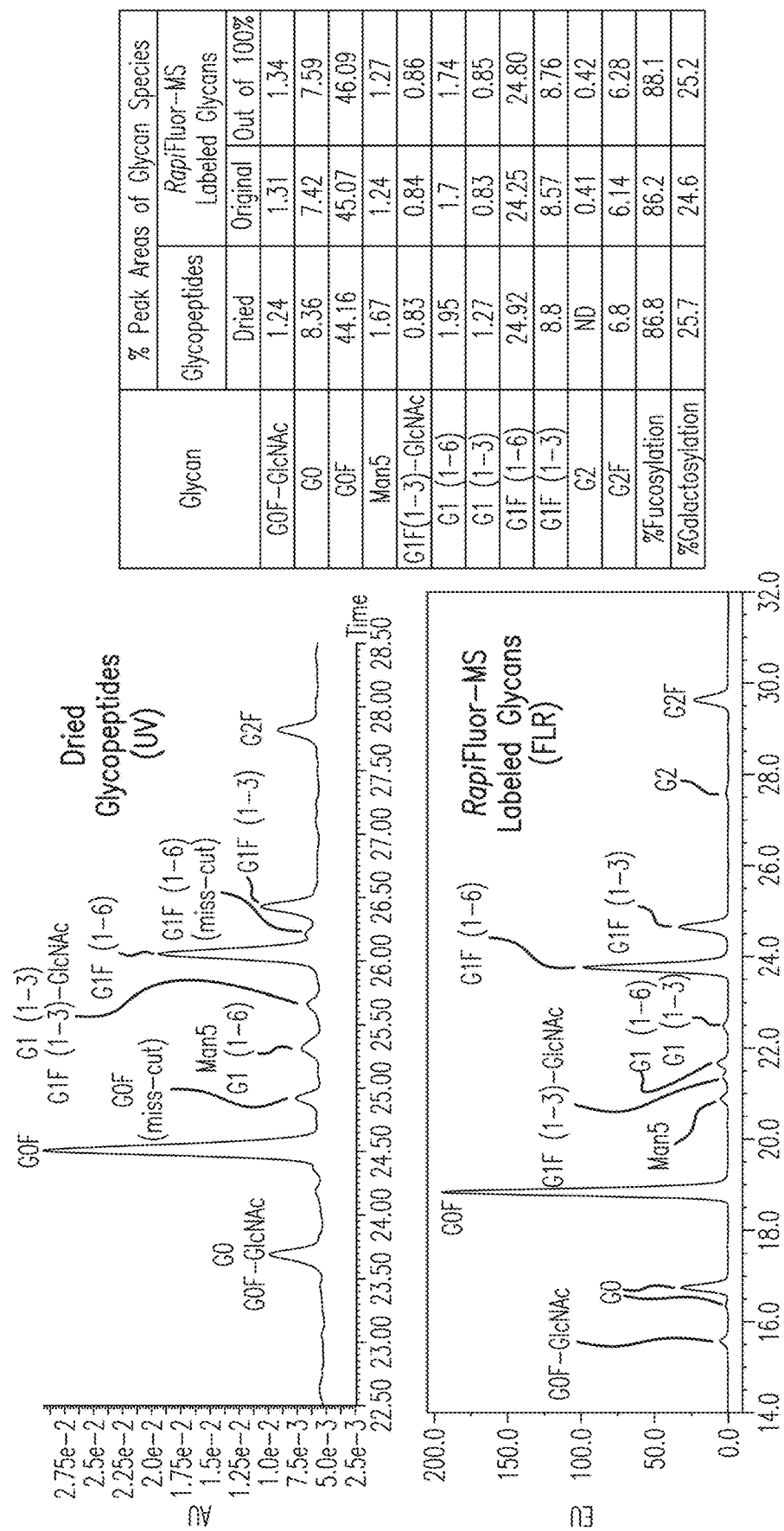
FIG. 19 shows a set of traces and a table demonstrating similar mAb3 glycoform quantitations by glycopeptide and released glycan analyses.

FIG. 19 is a set of traces and a table demonstrating similar mAb3 glycoform quantitations by glycopeptide and released glycan analyses.

Figure 20A:
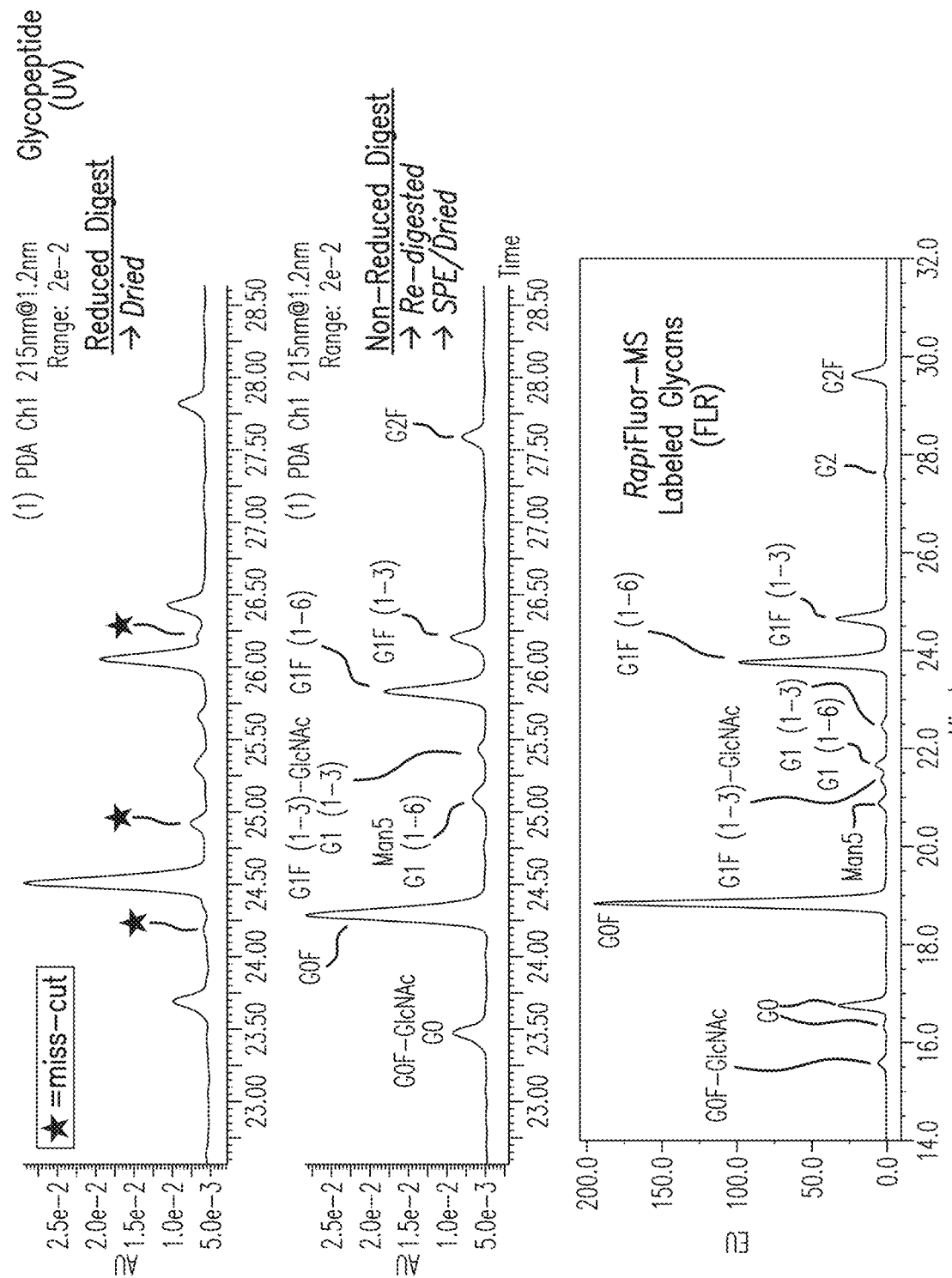

FIGS. 20A and 20B are a set of traces and a table demonstrating similar glycoform quantitations using reduced and non-reduced mAb3 tryptic digests by glycopeptide and released glycan analyses.

Figure 21:
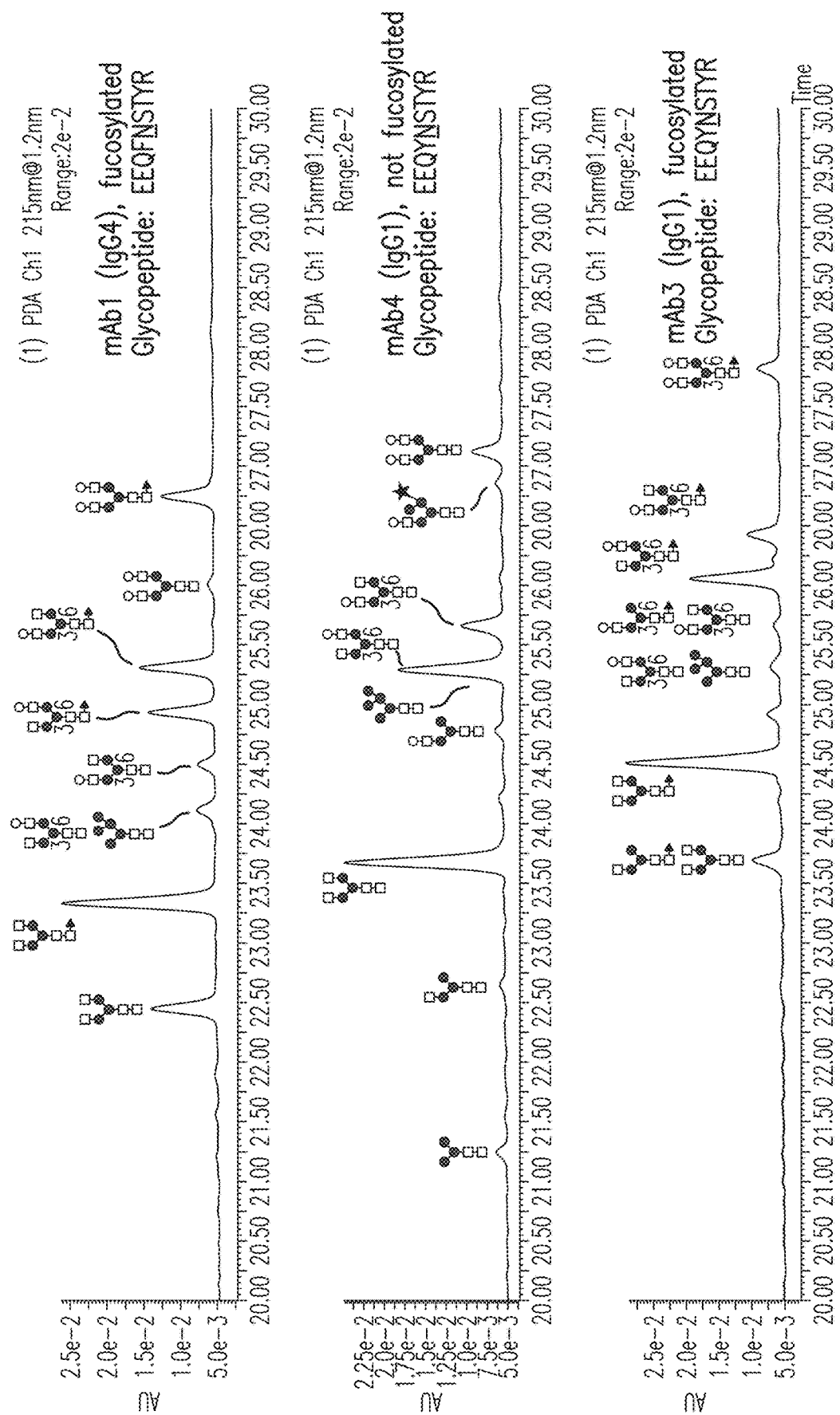
FIG. 21 shows a set of traces illustrating a comparison of separation of IgG1 and IgG4 glycopeptides, with and without fucosylation.

FIG. 21 is a set of traces showing a comparison of separation of IgG1 and IgG4 glycopeptides, with and without fucosylation.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of separating glycopeptides, comprising:
    contacting a sample comprising glycopeptides to a hydrophilic enrichment substrate under conditions that permit the glycopeptides to bind to the hydrophilic enrichment substrate;
    washing the hydrophilic enrichment substrate to remove non-glycopeptide contaminants from the hydrophilic enrichment substrate;
    eluting the glycopeptides from the hydrophilic enrichment substrate with an ammonium formate and acetonitrile (ACN) in water solution to create an enriched glycopeptide sample;
    applying the enriched glycopeptide sample to a separation column; and
    eluting the glycopeptides from the separation column, thereby separating glycopeptides in the sample.

2. The method of claim 1, wherein the hydrophilic enrichment substrate comprises a solid phase extraction (SPE) chromatography substrate.

3. The method of claim 1, wherein the hydrophilic enrichment substrate comprises a silica-based aminopropyl sorbent material.

4. The method of claim 1, wherein the ammonium formate and ACN in water solution comprises about 100-400 mM ammonium formate and about 2.5% to about 10% ACN in water.

5. The method of claim 1, wherein the hydrophilic enrichment substrate is washed with a formic acid and ACN wash solution comprising about 0.5% to about 5% formic acid by volume and about 85% to about 95% ACN by volume with the remainder water to remove non-glycopeptide contaminants.

6. The method of claim 5, wherein the formic acid and ACN wash solution comprises about 1% formic acid, about 9% $H_2O$, and about 90% ACN by volume.

7. The method of claim 1, wherein the separation column comprises a hydrophilic interaction (HILIC) column.

8. The method of claim 1, wherein eluting the glycopeptides from the separation column further comprises separating the glycopeptides into one or more fractions.

9. The method of claim 8, wherein separating the glycopeptides into one or more fractions comprises applying a mobile phase gradient to the separation column.

10. The method of claim 9, wherein the mobile phase gradient comprises about 10 mM ammonium formate, pH 4.5 to about 90% ACN with 10 mM ammonium formate, pH 4.5.

11. The method of claim 9, wherein the mobile phase gradient comprises about 0.05% TFA in $H_2O$ or about 0.045% TFA in ACN.

12. The method of claim 8, further comprising identifying the glycopeptides present in one or more of the fractions.

13. The method of claim 8, further comprising identifying a glycan associated with the glycopeptides present in one or more of the fractions.

14. The method of claim 8, wherein the glycopeptides are obtained from a monoclonal antibody.

15. The method of claim 14, further comprising digesting the monoclonal antibody with a protease.

16. The method of claim 15, wherein the protease comprises trypsin.

17. The method of claim 1, further comprising performing mass spectrometric analysis on the eluted glycopeptides.

18. The method of claim 1, further comprising glycosylation profiling at a glycopeptide level of the eluted glycopeptides.

19. The method of claim 1, further comprising prewashing the hydrophilic enrichment substrate with an acetonitrile (ACN) in water solution.

20. The method of claim 1, further comprising diluting the sample comprising glycopeptides in an ACN in water solution prior to contact with the hydrophilic enrichment substrate.

* * * * *